US007871406B2

(12) United States Patent
Nields et al.

(10) Patent No.: US 7,871,406 B2
(45) Date of Patent: Jan. 18, 2011

(54) METHODS FOR PLANNING AND PERFORMING THERMAL ABLATION

(75) Inventors: Morgan W. Nields, Englewood, CO (US); David E. Gustafson, North Bend, WA (US); Desikachari Nadadur, Issaquah, WA (US)

(73) Assignee: INTIO, Inc., Broomfield, CO (US)

( * ) Notice: Subject to any disclaimer, the term of this patent is extended or adjusted under 35 U.S.C. 154(b) by 1170 days.

(21) Appl. No.: 11/499,418

(22) Filed: Aug. 4, 2006

(65) Prior Publication Data
US 2008/0033420 A1   Feb. 7, 2008

(51) Int. Cl.
*A61B 18/04* (2006.01)
*A61B 18/18* (2006.01)
(52) U.S. Cl. .............................. 606/27; 606/32; 606/34
(58) Field of Classification Search ............. 606/32–40, 606/27
See application file for complete search history.

(56) References Cited

U.S. PATENT DOCUMENTS

| 4,341,220 A | | 7/1982 | Perry |
| 4,638,436 A | | 1/1987 | Badger et al. |
| 4,896,673 A | | 1/1990 | Rose et al. |
| 4,983,159 A | | 1/1991 | Rand |
| 5,348,551 A | * | 9/1994 | Spears et al. ................... 606/5 |
| 5,474,070 A | | 12/1995 | Ophir et al. |
| 5,536,267 A | | 7/1996 | Edwards et al. |
| 5,620,479 A | | 4/1997 | Diederich |
| 5,653,957 A | | 8/1997 | Miura et al. |
| 5,706,810 A | | 1/1998 | Rubinsky et al. |
| 5,782,762 A | * | 7/1998 | Vining ........................ 600/407 |
| 5,863,290 A | | 1/1999 | Gough et al. |

(Continued)

FOREIGN PATENT DOCUMENTS

JP   I-218466   8/1989

(Continued)

OTHER PUBLICATIONS

L. Curiel, et al., Experimental Evaluation of Lesion Prediction Modeling in the Presence of Cavitation Bubbles: Intended for High-Intensity Focused Ultrasound Prostate Treatment, Medical & Biological Engineering & Computing 2004, vol. 42, Sep. 26, 2003, 11 Pages.

(Continued)

*Primary Examiner*—Roy D Gibson
*Assistant Examiner*—Benjamin Lee
(74) *Attorney, Agent, or Firm*—Marsh Fischmann & Breyfogle LLP

(57) ABSTRACT

A thermal ablation system is operable to perform thermal ablation using an x-ray system to measure temperature changes throughout a volume of interest in a patient. Image data sets captured by the x-ray system during a thermal ablation procedure provide temperature change information for the volume being subjected to the thermal ablation. Intermediate image data sets captured during the thermal ablation procedure may be fed into a system controller, which may modify or update a thermal ablation plan to achieve volume coagulation necrosis targets. The thermal ablation may be delivered by a variety of ablation modes including radiofrequency ablation, microwave therapy, high intensity focused ultrasound, laser ablation, and other interstitial heat delivery methods. Methods of performing thermal ablation using x-ray system temperature measurements as a feedback source are also provided.

103 Claims, 10 Drawing Sheets

U.S. PATENT DOCUMENTS

| | | | |
|---|---|---|---|
| 6,190,378 B1 | 2/2001 | Jarvinen | |
| 6,216,027 B1 | 4/2001 | Willis et al. | |
| 6,231,565 B1 | 5/2001 | Tovey et al. | |
| 6,241,725 B1 | 6/2001 | Cosman | |
| 6,266,453 B1 | 7/2001 | Hibbard et al. | |
| 6,312,426 B1 | 11/2001 | Goldberg et al. | |
| 6,402,739 B1 | 6/2002 | Neev | |
| 6,435,714 B1 | 8/2002 | Bruder | |
| 6,506,189 B1 | 1/2003 | Rittman, III et al. | |
| 6,530,922 B2 | 3/2003 | Cosman et al. | |
| 6,542,767 B1 | 4/2003 | McNichols et al. | |
| 6,575,969 B1* | 6/2003 | Rittman et al. | 606/41 |
| 6,666,579 B2 | 12/2003 | Jensen | |
| 6,676,654 B1 | 1/2004 | Balle-Petersen et al. | |
| 6,684,097 B1* | 1/2004 | Parel et al. | 600/427 |
| 6,754,297 B2 | 6/2004 | James | |
| 6,757,412 B1 | 6/2004 | Parsons et al. | |
| 6,764,448 B2 | 7/2004 | Trahey et al. | |
| 6,842,502 B2 | 1/2005 | Jaffray et al. | |
| 6,881,214 B2 | 4/2005 | Cosman et al. | |
| 6,905,492 B2 | 6/2005 | Zvuloni et al. | |
| 6,914,959 B2* | 7/2005 | Bailey et al. | 378/65 |
| 6,951,544 B2 | 10/2005 | Trahey et al. | |
| 2001/0039417 A1* | 11/2001 | Harano et al. | 606/40 |
| 2002/0114499 A1* | 8/2002 | Breitenstein et al. | 382/128 |
| 2002/0168317 A1 | 11/2002 | Daighighian et al. | |
| 2002/0193686 A1 | 12/2002 | Gilboa | |
| 2003/0004413 A1 | 1/2003 | Inoue et al. | |
| 2003/0007601 A1* | 1/2003 | Jaffray et al. | 378/65 |
| 2003/0065313 A1 | 4/2003 | Koop et al. | |
| 2003/0125725 A1 | 7/2003 | Woodard et al. | |
| 2003/0130711 A1 | 7/2003 | Pearson et al. | |
| 2003/0171672 A1 | 9/2003 | Varghese et al. | |
| 2003/0208190 A1 | 11/2003 | Roberts et al. | |
| 2004/0015163 A1* | 1/2004 | Buysse et al. | 606/34 |
| 2004/0030227 A1 | 2/2004 | Littrup et al. | |
| 2004/0070584 A1 | 4/2004 | Pyo et al. | |
| 2004/0106870 A1 | 6/2004 | Mast | |
| 2005/0033160 A1 | 2/2005 | Yamagata et al. | |
| 2005/0038333 A1 | 2/2005 | Sra | |
| 2005/0059623 A1* | 3/2005 | Moonen | 514/44 |
| 2005/0065429 A1 | 3/2005 | Zhou | |
| 2005/0215899 A1 | 9/2005 | Trahey et al. | |
| 2005/0226375 A1 | 10/2005 | Eberhard et al. | |
| 2005/0228251 A1 | 10/2005 | Grabb et al. | |
| 2005/0249432 A1 | 11/2005 | Zou et al. | |
| 2006/0155267 A1 | 7/2006 | Berzak et al. | |
| 2006/0184163 A1 | 8/2006 | Breen et al. | |
| 2007/0197896 A1 | 8/2007 | Moll et al. | |
| 2007/0208327 A1 | 9/2007 | Rosemberg et al. | |

FOREIGN PATENT DOCUMENTS

| | | |
|---|---|---|
| WO | WO 0064536 | 11/2000 |
| WO | WO0243804 A1 | 6/2002 |

OTHER PUBLICATIONS

Mala et al. Magnetic Resonance Imaging-Estimated Three-Dimensional Temperature Distribution in Liver Cryolesions: A Study of Cryolesion Characteristics Assumed Necessary for Tumor Ablation. Cryobiology. vol. 43. pp. 268-275. 2001.

Samset et al. Neuronavigation in Intraoperative MRI. Clinical Paper. Computer Aided Surgery. vol. 4. pp. 200-207. 1999.

Samset et al. Temperature measurement in soft tissue using a distributed fibre Bragg-grating sensor system. Min Invas Ther & Allied Technol. vol. 10(2). pp. 89-93. 2001.

Samset et al. Validation of estimated 3D temperature maps during hepatic cryo surgery. Magnetic Resonance Imaging. vol. 19. pp. 715-721. 2001.

Samset et al. A Virtual Environment for Surgical Image Guidance in Intraoperative MRI. Computer Aided Surgery. vol. 7. pp. 187-196. 2002.

Samset et al. Stereotactic Target Localization Accuracy In The Interventional MRI. vol. 79. No. 3-4. pp. 191-201. 2002.

Samset et al. Image-Guided Stereotaxy in the Interventional MRI. Minim Invas Neurosurg. vol. 46. pp. 5-10. 2003.

Samset, Eigil. MRI-Guided Interventions Technological Solutions. Paper submitted to fulfill degree requirements. Rikshospitalet University Hospital. University of Oslo, Norway. 31 pages. 2003.

Altschuler et al. Optimized Interstitial PDT prostate treatment planning with the Cimmino feasibility algorithm. Med. Phys. vol. 332 No. 12, pp. 3524-3536. Dec. 2005.

Banovac et al. Precision targeting of liver lesions using a novel electromagnetic navigation device in physiologic phantom . . . Med. Phys. vol. 32 No. 8, pp. 2698-2705. Aug. 2005.

Bentzen et al. Isotherm mapping in hyperthermia using subtraction X-ray computed tomography. Radiotherapy and Oncology, 2, pp. 255-260. 1984.

Breakaway Imaging, LLC. O-Arm Imagin System 510(k). Apr. 2005.

Brock et al. Accuracy of finite element model-based multi-organ deformable image registration. Med. Phys. vol. 32 No. 6, pp. 1647-1659. Jun. 2005.

Buttemere et al. In vivo assessment of thermal damage in the liver using optical spectroscopy. Journal of Biomedical Optics. vol. 9, No. 5. Sep./Oct. 2004.

Chaney et al. Methods for image segmentation should be standardized and calibrated. Med. Phys. vol. 32 No. 12, pp. 3507-3510. Dec. 2005.

Chang et al. Thermal modeling of lesion growth with radiofrequency ablation devices. BioMedical Engineering Online. pp. 1-19. Aug. 2004.

Cheng et al. Blood perfusion and thermal conduction effects in Gaussian beam, minimum time single-pulse thermal therapies. Med. Phys. vol. 32 No. 6. pp. 311-317. Feb. 2005.

Djajaputra et al. Real-time 3D surface-image-guided beam setup in radiotherapy of breast cancer. Med. Phys. vol. 32 No. 1, pp. 65-75. Jan. 2005.

Fahey et al. Acoustic Radiation Force Impulse Imaging of Thermally- and Chemically-Induced Lesions in . . . Ultrasound in Med. & Biol., vol. 30, No. 3, pp. 321-328. Nov. 2004.

Fallone et al. Noninvasive thermometry with a clinical x-ray CT scanner. Med. Phys. vol. 9, No. 5, pp. 715-721. Sep./Oct. 1982.

Ford. C-T-based intraoperative dosimetry of prostate brachytherapy implants. Mentored Research Scholar Grant Application. pp. 1-33. Jul. 2003.

Freifeld et al. Use of Computed X-Ray Tomographic Data for Analyzing the Thermodynamics of a . . . Lawrence Berkeley Nat'l Laboratory. Paper LBNL-49889. Feb. 28, 2002.

Gebhart et al. Dynamic, three-dimensional optical tracking of an ablative laser beam. Med. Phys. vol. 32, No. 1, pp. 209-220. Jan. 2005.

Goldberg et al. Image-guided Tumor Ablation: Standardization of Terminology and Reporting Criteria. Radiology. vol. 235, No. 3, pp. 728-739. Jun. 2005.

Hammerich. Ablative therapies for cancer treatment. Medical Physics Seminar. pp. 1-60. Oct. 27 2003.

Hu et al. An approximate short scan helical FDK cone beam algorithm based on nutating curved surfaces satisfying the . . . Med. Phys. vol. 32, No. 6, pp. 1529-1536. Jun. 2005.

Hummel et al. Design and application of an assessment protocol for electromagnetic tracking systems. Med. Phys. vol. 32, No. 7, pp. 2371-2379. Jul. 2005.

Jain et al. FTRAC—A robust fluoroscope tracking fiducial. Med. Phys. vol. 32, No. 10, pp. 3185-3198. Oct. 2005.

Jenne et al. CT On-Line Monitoring of HIFU Therapy. 1997 IEEE Ultrasonics Symposium. Canada. vol. 2, pp. 1377-1380. Oct. 1997.

Jin et al. Imaging of high-intensity focused ultrasound-induced lesions in soft biological tissue using thermoacoustic . . . Med. Phys. vol. 32, No. 1, pp. 5-11. Jan. 2005.

Lauritsch. Fundamentals of static 2D . . . Interdisciplinary Center for Scientific Computing, Tutorial on Computed Tomography, U. of Heidelberg, Germany. pp. 1-54. Dec. 2003.

Lin et al. Optically tunable nanoparticle contrast agents for early cancer detection . . . J. of Biomedical Optic. vol. 10, No. 6, pp. 064035-1-064035-10. Nov./Dec. 2005.

Lizzi et al. Radiation-force technique to monitor lesions during ultrasonic therapy. Ultrasound in Medicine & Biology. vol. 29 Issue 11, pp. 1593-1605. Nov. 2003.

McAleavey et al. Estimates of echo correlation and measurement bias in acousti . . . IEEE Trans Ultrason Ferroelectr Freq Control. vol. 50, No. 6, pp. 631-641. Jun. 2003.

Minhaj et al. X-ray monitoring of laser interstitial thermotherapy (LITT) in ex vivo porcine tissue. Proc. SPIE. vol. 4244, pp. 500-507. May 2001.

Moonen. MR temperature mapping in local drug delivery and thermotherapy. Medica Mundi. vol. 44, No. 3, pp. 34-42. Nov 2000.

Nightingale et al. Acoustic radiation force impulse imaging: in vivo . . . Ultrasound in Medicine & Biology. vol. 28, Issue 2, pp. 227-235. Feb. 2002.

Nightingale et al. Acoustic radiation force impulse imaging of in vivo vastus medialis muscle under varying . . . Ultrason Imaging. vol. 24, No. 2, pp. 100-108. Apr. 2002.

Nightingale et al. Observations of tissue response to acoustic radiation force: opportunities for imaging. Ultrason Imaging. vol. 24, No. 3, pp. 129-138. Jul. 2002.

Ning et al. Flat panel detector-based cone beam computed tomography with a circle-plus-two arcs data acquisition orbit . . . Med. Phys. vol. 30, No. 7, 1694-1705. Jul. 2003.

Pan et al. Image reconstruction in peripheral and central regions-of-interest and data redundancy. Med. Phys. vol. 32, No. 3, pp. 673-684. Mar. 2005.

Pappas et al. improved targeting device and computer navigation for accurate placement of brachytherapy needles. Med. Phys. vol. 32, No. 6, pp. 1796-1801. Jun. 2005.

Pizer et al. A method and software for segmentation of anatomic object ensembles by deformable m-reps. Med. Phys. vol. 32, No. 5, pp. 1335-1345. May 2005.

Pollard et al. Contrast-assisted Destruction-replenshment Ultrasound for the Assessment of . . . Technology in Cancer Research & Treatment, vol. 1, No. 6, pp. 459-470. Dec. 2002.

Ragan et al. Semiautomated four-dimensional computed tomography segmentation using deformable models. Med. Phys. vol. 32, No. 7, pp. 2254-2261. Jul. 2005.

Rohlfing et al. Progressive attentuation fields: fast 2D-3D image registration without precomputation. Med. Phys. vol. 32, No. 9, pp. 2870-2880. Sep. 2005.

Ross et al. Curvilenear transurethral ultrasound applicator for selective prostate thermal therapy. Med. Phys. vol. 32, No. 6, pp. 1555-1565. Jun. 2005.

Salas et al. Thermal Analysis of Lasar Interstitial Thermotherapy In Ex-Vivo Fibro-Fatty Tissue Using Exponential functions. Phys. Med. Biol. vol. 49, pp. 1609-1624. Apr. 2004.

Sandison et al. X-ray CT monitoring of iceball growth and thermal distribution during cryosurgery. Phys. Med. Biol. vol. 43, pp. 3309-3324. 1998.

Shah et al. Chord-based versus voxel-based methods of electron transport in the skeletal tissues. Med. Phys. vol. 32, No. 10, pp. 3151-3159. Oct. 2005.

Sharpe et al. The stability of mechanical calibration for a kV cone beam computed tomography system integrated with . . . Med. Phys. vol. 33, No. 1, pp. 136-144. Jan. 2006.

Shih et al. The impact of thermal wave characteristics on thermal dose distribution during thermal therapy . . . Med. Phys. vol. 32, No. 9, pp. 3029-3036. Sep. 2005.

Siewerdsen et al. Volume CT with a flat-panel detector on a mobile, isocentric C-arm: Pre-clinical . . . Med. Phys. vol. 32, No. 1, pp. 241-254. Jan. 2005.

Taschereau et al. Monte Carlo simulations of dose from microCT imaging procedures in a realistic mouse phantom. Med. Phys. vol. 33, No. 1, pp. 216-224. Jan. 2006.

Thomas et al. Patient specific treatment verifications for helical tomotherapy treatment plans. Med. Phys., vol. 32, No. 12, pp. 3793-3800. Dec. 2005.

Trevino. New ultrasound technique palpates breast lesions remotely. Diagnostic Imaging Online. pp. 1-2. Apr. 22, 2002.

Turgeon et al. 2D-3D registration of coronary angiograms for cardiac procedure planning and guidance. Med. Phys. vol. 32, No. 12, pp. 3737-3749. Dec. 2005.

Tyreus et al. Effect of applicator diameter of lesion size from high temperature interstitial ultrasound thermal therapy. Med. Phys. vol. 30, No. 7, pp. 1855-1863. Jul. 2003.

Yan et al. Tilted plane Feldkamp type reconstruction algorithm for spiral cone beam CT. Med. Phys. vol. 32, No. 11, pp. 3455-3467. Nov. 2005.

Ye et al. Filtered backprojection formula for exact image reconstruction from cone-beam data along a general scanning curve. Med. Phys. vol. 32, No. 1, pp. 42-48. Jan. 2005.

Yu et al. Exact BPF and FBP algorithms for nonstandard saddle curves. Med. Phys. vol. 32, No. 11, pp. 3305-3312. Nov. 2005.

Yue et al. A method to implement full six-degree target shift corrections for rigid body in image-guided radiotherapy. Med. Phys. vol. 33, No. 1, pp. 21-31. Jan. 2006.

Zhao et al. A unified framework for exact cone-beam reconstruction formulas. Med. Phys. vol. 32, No. 6, pp. 1712-1721. Jun. 2005.

Zou et al. Pi-line based image reconstruction in helical cone-beam computed tomography with a variable pitch. Med. Phys. vol. 32, No. 8, pp. 2639-2648. Aug. 2005.

* cited by examiner

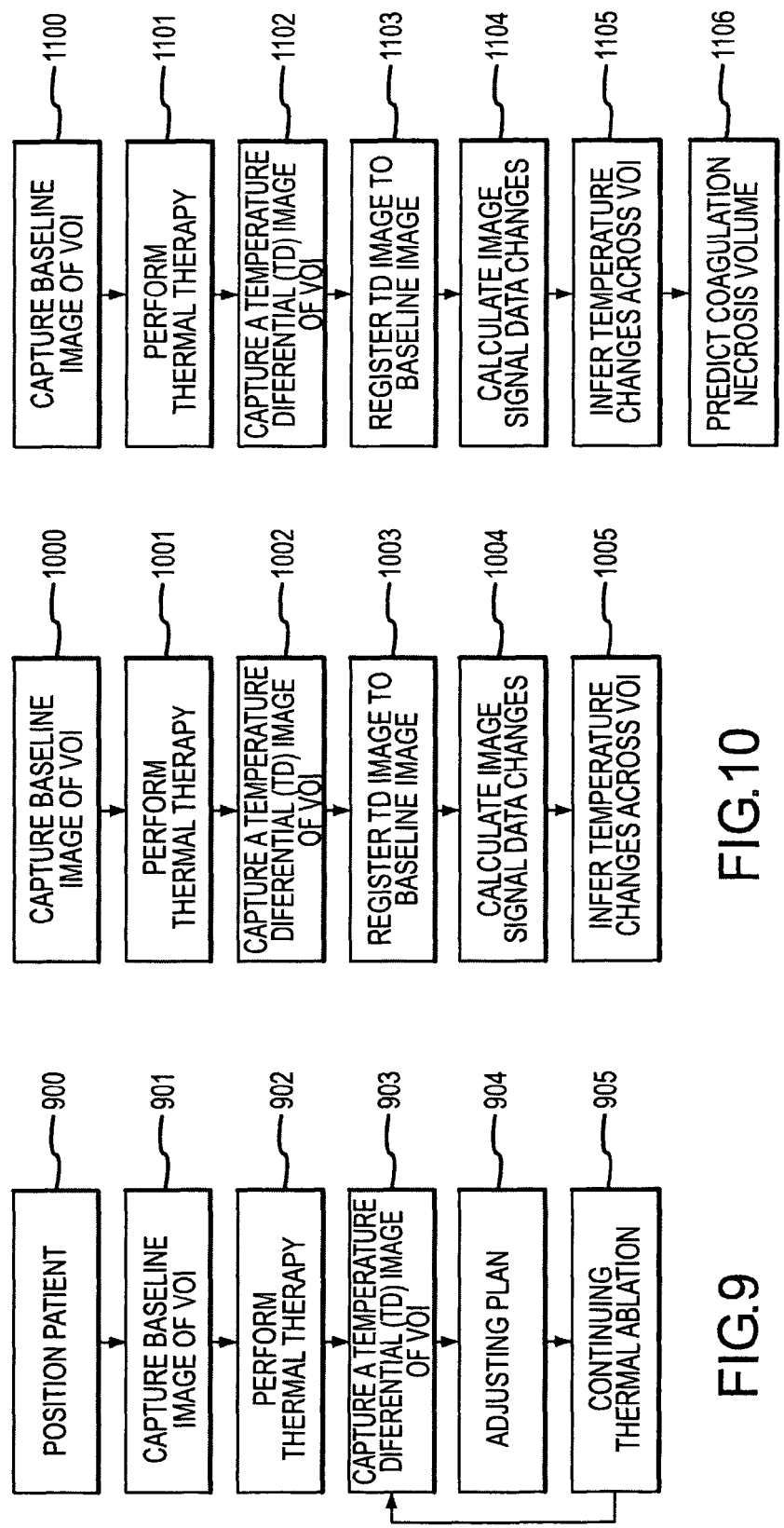

METHODS FOR PLANNING AND PERFORMING THERMAL ABLATION

FIELD OF THE INVENTION

The present invention relates to thermal ablation systems and methods and, in particular, to improved systems and methods for planning and performing thermal ablation.

BACKGROUND OF THE INVENTION

Thermal ablation involves the creation of temperature changes sufficient to produce coagulation necrosis in a specific volume of tissue within a patient, typically one or more benign and/or cancerous tumors. In the case of the application of temperatures elevated to above about 50 degrees C., the proper application of heat can result in tissue destruction primarily due to the destruction of proteins within the cells. In the case of reducing the temperature of the targeted area, cycles of proper freezing and thawing can result in tissue destruction primarily due to cell rupture.

Traditional methods of treating cancerous tumors include surgery to physically remove the tumor, chemotherapy to provide systemic treatment by chemical means or radiation, which produces apoptosis in the cells treated with radiation. Frequently these methods are combined to produce the greatest chance of cure. Although these procedures may be life saving, there are serious side effects and risks associated with radiation, chemotherapy, and surgery, any of which may significantly affect patient quality of life.

As a result, there is increasing interest and development of non-invasive or minimally invasive methods to kill tumor cells. In particular, thermal ablation is being investigated as an alternative and/or supplement to traditional methods of tumor destruction. Several methods have been developed and are being developed for various forms of cancer including, among others, cancers of the breast, prostate, lung, kidney, and liver. Methods of introducing localized heat include Radio Frequency Ablation (RFA), microwave therapy, extracorporeal or direct focused ultrasound, laser ablation, and other interstitial heat delivery methods including therapeutic ultrasound applicators. These methods may be applied percutaneously or extracorporeally. Cryoablation, i.e. the freezing of tissue to produce necrosis, is also being used to treat tumors. A significant challenge in ablation therapy is to provide adequate treatment to the targeted tissue while sparing the surrounding structures from injury.

RFA uses electrical energy transmitted into a VOI through an electrode to generate heat in the area of the electrode tip. The radio waves emanate from the non-insulated distal portion of the electrode. The introduced radiofrequency energy causes ionic agitation in the area surrounding the electrode as the current flows from the electrode tip to ground. The resulting agitation causes the temperature in the area surrounding the electrode tip to rise. Temperature calibration or measurement devices, for example thermocouples, in the electrode may provide feedback and allow precise control of the temperatures produced at the electrode tip, while other devices rely on tissue impedance changes to indicate tissue thermal injury. In microwave therapy, applicators function as antennae that concentrate the transmitted microwave energy around the antennae. As in microwave ovens, polar molecules attempt to align themselves with the shifting electromagnetic fields resulting in movement, friction and subsequent heating of the area around the antennas.

Extracorporeal or direct focused ultrasound ablation uses focused sound waves to deliver enough energy to heat a specific volume of tissue to cause coagulation necrosis. To produce coagulation necrosis in larger volumes of tissue the target point is rastered across the target area. Prior to being focused, the sound waves pass through tissue without causing significant heating, only causing destructive heat around the focal point. Therefore, extracorporeal focused ultrasound ablation may be performed without an incision. Laser ablation uses high intensity light to raise the temperature of a target area to produce coagulation necrosis in that area. Generally, needles or applicators containing thin optical fibers are interstitially placed within a tumor. The intense light is transmitted through the optical fibers to the applicator tip and scattered into the targeted area.

Various methods of thermal ablation are being investigated for various types of cancer and various tumor types. For example, cryoablation, focused ultrasound ablation, RFA, microwave thermal ablation, and interstitial self-regulating thermal rods, have all been the subject of studies of the treatment of prostate cancer. However, significant challenges remain with respect to an approach for planning and performing thermal ablation.

SUMMARY OF THE INVENTION

The present invention is directed toward methods and apparatuses for the planning and performing of a thermal ablation procedure. The planning aspect may comprise inputting a target volume where coagulation necrosis is desired and, based on characteristics of the target volume and surrounding area, generating a set of thermal ablation parameters to produce the desired coagulation necrosis. The parameters may, for example, include selecting a mode or modes of thermal ablation delivery from a plurality of available modes. The planning may also include simulating the thermal ablation procedure according to the generated parameters. The thermal ablation performance aspect comprises monitoring the progress of thermal ablation and comparing the progress of the thermal ablation procedure to a thermal ablation plan, e.g. to assess the prospective outcome of the procedure. In turn, in certain instances, the procedure may be modified accordingly to achieve the overall goals of the thermal ablation procedure. The planning aspect may be performed prior to the performance of thermal ablation and/or during a thermal ablation procedure. In the case of planning occurring during thermal ablation, the planning may include modifying an existing plan based on the progress of the thermal ablation or developing a new plan based on the progress of the thermal ablation.

The term "thermal ablation" used herein includes the application of energy to increase the temperature of a targeted region or the application of cryoablation to reduce the temperature of a targeted region, or some combination thereof. The term "thermal ablation procedure" used herein refers to a single intervention episode that consists of one or more thermal ablations. For example, a thermal ablation procedure may include positioning a patient, imaging a Volume Of Interest (VOI) in the patient multiple times, performing thermal ablation multiple times, and removing any applicators after the thermal ablations are completed. "Thermal ablation treatment" consists of one or more thermal ablation procedures and as such may take place at several discreet points in time over several days or more, similar to how chemotherapy may take place over the course of several days or more. The term "applicator" used herein is used to indicate any device that may be used to deliver thermal ablation. The delivery of thermal ablation using an applicator may take the form of delivering energy to a targeted volume of a patient and/or the removal of energy (e.g. in the case of cryoablation) from a targeted volume of a patient. Therefore, for example, RFA electrodes and microwave antennas are two specific types of applicators.

A primary step in the planning of a thermal ablation procedure is to obtain an accurate image data set of the VOI, which contains the tumor or structure to be ablated. The inventors have recognized that there exists a need for, and have provided, the integration of multiple imaging modalities to produce a full thermal properties profile of a VOI in a patient. In this context, "thermal properties profile" means a thermal data set associating one or more physical properties of the VOI, for example including one or more of density, thermal conductivity, specific heat and electrical conductivity of structures and tissue within the VOI, with an array of three-dimensional spatial locations within the VOI. The thermal properties profile may be generated through computational techniques such as finite element analysis.

The present inventors have also recognized the need for, and have provided an improved thermal ablation planning system that is capable of modeling multiple modes of thermal ablation delivery. Therefore, the present invention is capable of integrating multiple images produced by differing imaging modalities along with the thermal properties profile of structures within the VOI to generate a model of the VOI. This model can then be used as a basis for simulating the effects of various thermal ablation procedures. A physician may demarcate regions or volumes within the model that are to be subjected to thermal ablation to produce coagulation necrosis. The term "physician," as used herein, may include one or more physicians, practitioners, interventionalists, users or any other specialty or individual who may be involved in planning and/or performing thermal ablation. The physician may also indicate regions or volumes within the model whose exposure to effects of the thermal ablation is to be limited. These indications may further include desired temperature limits, time limits or a combination of temperature and time limits.

The model of the VOI and the physician inputs may be used to develop a proposed plan for the thermal ablation procedure. This plan may be in four dimensions: a spatial three-dimensional representation of the expected temperature profile throughout the VOI at any given time during the planned thermal ablation. The proposed plan may recommend a particular mode or modes for delivery of the thermal ablation. The planning system may choose the particular mode or modes from a plurality of modes available for use by the physician. Alternatively, the choice of thermal ablation delivery mode may be made by the physician prior to generating the thermal ablation plan. After the plan is generated by the system, the physician may alter or substitute modes for delivery of the thermal ablation. The system may then regenerate a new proposed plan for the thermal ablation procedure which may be reviewed by the physician. In this manner, the physician is able to simulate the effects of different modes for delivery of the thermal ablation with respect to the thermal ablation goals and limitations inputted by the physician.

Similarly, the thermal ablation planning system may suggest thermal ablation applicator type, quantity, placement, and power levels throughout the proposed thermal ablation procedure. The plan itself may be stored in a memory module after creation and accessed prior to the performance of the thermal ablation procedure. The memory module may be, for example, a networked computer that may be accessed from the surgical area or a portable memory device that may be brought into the surgical area and accessed by a local computer system. As with the mode of therapy delivery discussed above, these aspects of the thermal ablation plan may be altered or substituted by the physician. After any change, the system may regenerate the thermal ablation plan and display the effects of the change to the physician. Planned in-process monitoring methodologies and intervals may also be suggested by the thermal ablation planning system and may also be altered or substituted by the physician.

In addition to the parameters discussed above, other parameters may be generated and included in the thermal ablation plan. By way of example, the thermal ablation plan generated during the planning stage may include any one or more of the following:

expected temperature changes throughout the VOI as a function of time during the thermal ablation procedure;
target coagulation necrosis volume;
planned coagulation necrosis volume;
thermal ablation applicator quantity;
thermal ablation applicator type (in the case of a single applicator) or types (in the case where multiple applicators are required);
thermal ablation applicator power level (for each applicator);
thermal ablation applicator position (for each applicator);
thermal ablation applicator target (for each applicator);
temperature differential image triggering parameters (used to determine when a temperature differential image should be captured); and
supplemental imaging modalities.

Each of the above parameters may be contained in the plan as a function of time during the thermal ablation procedure. For example, the plan may include changing applicator power level from a first level to a second level two minutes into the procedure. Other parameters that may also be part of the plan include:

patient positioning; and
temperature differential image capture schedule.

Other parameters typically part of planning a surgical procedure may also be contained within the plan, such as the location and time of the procedure, surgical personnel required and medications or anesthesia to be administered.

The target coagulation necrosis volume may differ from the planned coagulation necrosis volume for several reasons. For example, the target coagulation necrosis volume may be a cancerous tumor. However, in order to ensure complete coagulation necrosis of the target volume, some surrounding tissue may need to be subjected to temperatures that will cause coagulation necrosis. Therefore, the final planned coagulation necrosis volume in this case may be slightly larger than the target necrosis volume.

The present inventors have recognized the need for, and have provided, a treatment methodology with improved in-process monitoring and process updating. An x-ray imaging system may be used during the thermal ablation to provide in-process images of thermal profiles within the VOI. The x-ray imaging system may also provide guidance for applicator placement within the VOI and the locations of structures (such as organs, veins, arteries, etc.) within the VOI. The in-process images may be two-dimensional or three-dimensional. The in-process images may be generated using Computed Tomography (CT). The imaging may be performed using conventional CT, where a VOI is imaged by indexing the position of the x-ray scanner relative to the patient between the capturing of two-dimensional slices. The imaging may be performed using helical CT where the patient is translated through the field of view of the x-ray scanner while an x-ray source and x-ray detector or rotated about the VOI.

The imaging may be performed using other CT scanning methodologies where novel scan paths are incorporated.

Novel imaging reconstruction techniques associated with the novel scan paths may allow an x-ray CT scanner, moving in non-conventional, non-helical scan paths, to create three-dimensional CT images of the VOI. Novel imaging reconstruction techniques may also reduce image capture times. Novel image reconstruction algorithms may be used. To further reduce image capture times, the CT scanners may possess multi-detector cone-beam (CB) volume imaging capability, e.g. conical x-ray beams may be used and detected by two-dimensional flat-panel x-ray detectors.

As used herein, the term "CT" refers to a process or system operable to aggregate multiple individual readings or a stream of readings into composite images. Therefore, for example, an x-ray CT scanner refers to an x-ray scanner capable of aggregating multiple x-ray measurements into a composite image. Additionally, as used herein, the term "scanner" refers to a device operable to move imaging means relative to an area or volume of interest to be imaged. Subsequently, the term "x-ray scanner" refers to a device operable to move an x-ray source and detector relative to an area or volume of interest to be imaged. Accordingly, the term "x-ray CT scanner" refers to a device operable to move an x-ray source and detector relative to an area or volume of interest for scanning and generating a composite image of that area or volume.

An x-ray system comprising an arcuate support member may be used to perform the in-process temperature monitoring, wherein at least one pair of an x-ray source and an x-ray detector are arranged in an opposed relationship on the arcuate support member and are operable to be rotated about and/or translated in relation to the VOI within the patient. An example of such a system is an x-ray system known to those skilled in the art of medical imaging wherein the x-ray source and x-ray detector are mounted on the ends of a C-shaped member. Such an x-ray system, which provides improved access to the patient during image capture, may reduce the amount of or eliminate patient movement that may be required during the acquisition.

As used herein, the term "C-arm" refers to any open or openable imaging system including, for example, x-ray systems with a C-shaped member as described above. The present invention is intended to include x-ray systems capable of imaging a VOI in patient where opposed x-ray sources and detectors are mounted to a support member which is not a permanent closed ring through which the patient must be passed in order to perform imaging. Therefore, other open or openable configurations, e.g. those known in the art as U-arm or O-arm (which is described below) systems are included within the definition of C-arm as used herein. The x-ray system may be isocentric in that it may be operable to rotate the opposed x-ray sources and detectors about a single point. The x-ray system may be non-isocentric.

As discussed above, the x-ray system may use conical beams. The x-ray system may be an x-ray scanner. The x-ray system may use CT. The x-ray system may include a C-arm. The x-ray system may be operable to generate three-dimensional temperature maps of a VOI. Any two or more of these features may be combined. For example, the x-ray system may be an x-ray CBCT C-arm scanner which refers to an open or openable system that uses an x-ray source which produces a conical beam which can be detected by a two-dimensional detector array, wherein the x-ray source and detector are operable to be scanned relative to a VOI to produce a three-dimensional image and temperature map of the VOI. Accordingly, such a system may be used to monitor temperature changes during a thermal ablation procedure. Additionally, the monitored temperature changes may be compared to expected temperature changes in a thermal ablation plan.

Acoustic Radiation Force Impulse (ARFI) ultrasound imaging may be used in lieu of or in conjunction with x-ray CT imaging to determine tissue stiffness within the VOI. ARFI imaging involves the application of a force impulse in the form of an acoustic wave to the VOI. The movement of structures within the VOI in reaction to the impulse is measured with ultrasound equipment. The structures within the VOI will react differently to the stress imposed by the impulse. These differences can then be measured by the ultrasound equipment and correlated to structure properties including temperature.

Ultrasound imaging may be used to create images of elastic properties of tissue using elastography or strain imaging applications. In these applications, an external force (typically either robotically or manually applied) is used to compress tissue. Ultrasound images are acquired during compression and relaxation, taking advantage of speed of sound changes with tissue density. Tissue properties similar to those measured with ARFI ultrasound imaging are derived. Ultrasound elastography may be used in lieu of or in conjunction with x-ray CT imaging to determine tissue stiffness within the VOI. The structures within the VOI will react differently to the stress imposed by the pressure, similar to the pressure pulse generated by ARFI. These differences can then be measured by the ultrasound equipment and correlated to structural tissue properties, such as Young's modulus, and may include temperature.

Elastography and/or ARFI may be used to detect changes within the VOI due to the application of thermal ablation. These changes may indicate temperature or other changes in the VOI such as coagulation. Once these changes surpass a predetermined level, an x-ray CT image may be triggered.

The temperature profile determined by the in-process imaging may be compared to the expected temperature profile of the thermal ablation plan. The plan can then be modified accordingly to meet the overall goals of the thermal ablation procedure inputted by the physician. The physician may be presented with 3-D images of the thermal profiles of both the plan and the in-process measurements. These images may include a prediction of cell death based on the application of temperature changes to the VOI for a specified period of time. These images may also include the positioning of any applicators or devices within the VOI. The plan may be updated automatically by altering power levels of the thermal ablation applicators. The plan may also be updated by indicating new applicator positions and/or quantities. These new applicator specifications may be achieved by physician repositioning or by automatic repositioning means.

The present inventors have also recognized a need for, and have provided, post-operative diagnostic tools to compare original condition, post operation expected results and actual post operation results to develop further therapy plans for the thermal ablation patient and to improve therapy prediction capabilities in general.

Advantages of employing thermal ablation procedure plans and dynamic intra-procedural controls of thermal ablation applicators as disclosed herein include more accurate thermal ablation with less morbidity, shorter overall procedure times, lower procedure costs, and lowered anesthesia risk to the patient. Furthermore, lesions close to critical structures such as bowel, ureter, spinal canal, or large vessels including the aorta or vena cava which carry heat away in the blood (or may carry heat to the ablation site in the case of cryoablation) may be safely addressed by ablation, increasing the number of patients that may be helped by thermal ablation.

According to one aspect there is provided an apparatus for performing thermal ablation within a VOI in a patient wherein the apparatus includes an x-ray system operable to measure temperature changes across the VOI in the patient. The apparatus may be capable of measuring temperature changes for each spatial location in an array of spatial locations throughout the VOI. In one embodiment, each spatial location may be a voxel representing a volume of at most 1 cm$^3$. In another embodiment, each voxel may represent a volume of at most 1 mm$^3$.

The x-ray system of the present aspect may be an x-ray CT scanner. The x-ray CT scanner may be operable to emit and detect a plurality of x-rays incident on the VOI in a plurality of orientations and from signals generated by the detection of x-rays generate a data set depicting the VOI using computed tomography. Furthermore, the x-ray system may be an x-ray C-arm CT scanner which may be operable to be positioned around the VOI in a plurality of orientations. In one embodiment, the x-ray beam from the x-ray source may be conical and the x-ray detector may include a two-dimensional x-ray detector array. The conical beam may illuminate an entire three-dimensional volume with each illumination and detection cycle.

According to another aspect there is provided an apparatus for performing thermal ablation within a VOI in a patient wherein the apparatus includes at least one thermal ablation applicator. The thermal ablation applicator or applicators may be radio frequency ablation electrodes, laser ablation fibers, microwave antennas, extracorporeal focused ultrasound transducers, direct focused ultrasound transducers, cryoprobes, and interstitial ultrasound therapy systems. Other types of applicators known to those skilled in the art may also be used. In one embodiment, the apparatus includes one thermal ablation applicator wherein the applicator may be any one of the aforementioned types of applicators. In another embodiment, multiple thermal ablation applicators may be included in the apparatus. These multiple applicators may all be of the same type (i.e. multiple instances of one type of applicator) or of a plurality of different types of applicators (i.e. single or multiple instances of multiple types of applicators). The apparatus may include at least one robotic arm operable to automatically position some or all of the thermal ablation applicators.

In another aspect there is provided an apparatus for performing thermal ablation within a VOI in a patient wherein the apparatus includes a controller operable to compare measured temperature changes across the VOI measured by the x-ray system to expected temperature changes contained in a thermal ablation plan. The plan may include expected temperature changes at each spatial location as a function of time during the thermal ablation procedure. The controller may include a registration module operable to register three-dimensional images of the VOI to other three-dimensional images of the VOI. In one embodiment, artificial fiducial markers may be included in the apparatus where the artificial fiducial markers may be locatable by the x-ray system. These fiducial markers may be internal to the patient and may have been implanted into the patient in order to assist in the registration of images. The fiducial markers may be external to the patient, such as markers placed on the skin of the patient, to assist in the registration of images. A combination of internal and external fiducial markers may be included in the apparatus. The registration module may utilize the fiducial markers to assist in the registration process. The registration process may also use only natural structures as fiducial markers within the VOI to register multiple images to each other. Such natural structures may include, but are not limited to, organs, bones, and blood vessels. The registration process may also use a combination of artificial and natural fiducials to register images to one another.

In embodiments including an x-ray CT scanner, the apparatus may be operable to generate two-dimensional images of the measured temperature changes corresponding to a physician selected two-dimensional plane. The apparatus may be operable to generate images of the measured temperature changes in three spatial dimensions. Furthermore, the apparatus may be operable to generate sequential images, representing sequential points in time, of the measured temperature changes in three spatial dimensions.

In another aspect, the system controller may be operable to trigger an image capture sequence by the x-ray system. The controller may be operable to adjust at least one characteristic of any or all of the thermal ablation applicators in closed-loop control. The adjustment of characteristics may be as per a thermal ablation plan or in response to temperature measurements made by the apparatus. The adjustments to the thermal ablation applicators may be to applicator power, applicator position, applicator type, applicator quantity, or any combination thereof. The controller may make the adjustments automatically or the controller may indicate to a physician any adjustments to the thermal ablation applicators that are required. Also, the apparatus may utilize a combination of automatic and manual adjustments.

In yet another aspect there is provided an apparatus for performing thermal ablation within a VOI in a patient wherein an ultrasound imaging device is included operable to generate images of the VOI in the patient. The ultrasound imaging device may be operable to capture ultrasound images of the VOI or portions of the VOI between imaging cycles of the x-ray system. The ultrasound imaging device may be operable to determine the location of any thermal ablation applicator within the VOI. The ultrasound imaging device may be operable to measure changes within the VOI that can then be used to trigger image capture cycles by the x-ray system.

The ultrasound imaging device may be capable of operating in an ARFI imaging mode. The ARFI imaging mode may be operable to detect thermal ablation induced changes in the VOI. The ARFI imaging mode may be operable to trigger an image capture by the x-ray system. The ultrasound imaging device may be capable of elastography imaging. The ultrasound imaging device with elastography imaging capabilities may be operable to detect thermal ablation induced changes in the VOI. The ultrasound imaging device with elastography imaging capabilities may be operable to trigger an image capture by the x-ray system.

According to one aspect there is provided a method for performing a thermal ablation procedure within a VOI in a patient that includes capturing a baseline digital image of the VOI in the patient with an x-ray system. In this aspect, the baseline digital image includes a first set of detected image signal data corresponding with an array of spatial locations substantially throughout the VOI.

According to another aspect, the capturing of the baseline digital image includes illuminating the VOI with x-rays. The illumination of the VOI may be accomplished with a cone shaped beam. The illumination of the VOI may be accomplished with a dynamically shaped beam of x-rays where the beam may be shaped by at least one multi-leaf collimator. In accordance with another aspect, the capturing of the baseline digital image includes detecting a plurality of portions of the x-rays that passed through the VOI. The illuminating and detecting may be performed by an x-ray CT scanner. The x-ray CT scanner may be a C-arm x-ray CT scanner.

In accordance with another aspect, the capturing of the baseline digital image includes at least partially generating the baseline digital image based on the detected x-rays. The baseline digital image may include information obtained through a supplemental imaging modality. The supplemental imaging modality may utilize image enhancing software. The supplemental imaging modality may also employ visualization software to better communicate with the physician regarding the structure and features of the VOI. In one embodiment of the present aspect, the baseline digital image is also generated using one or more of the following imaging modalities: ultrasound, ultrasound with ARFI capabilities, ultrasound with elastography capabilities, PET, SPECT, and MRI. These additional imaging modalities may be enhanced by using contrast agents. In another embodiment, the capturing of the baseline digital image includes calibrating the baseline digital image. This calibration may include measuring the temperature of at least a first spatial location within the VOI and correlating the measured temperature to the baseline digital image at the same spatial location.

In another embodiment, the baseline digital image may be spatially filtered. The filter used may be a Gaussian filter. In another embodiment, software may be employed to automatically identify structures within the baseline digital image. These structures may include, but are not limited to, organs, vessels, and tumors. In one embodiment of the method, each spatial location may be a voxel representing a volume of at most 1 $cm^3$. In another embodiment, each voxel may represent a volume of at most 1 $mm^3$. The method may further include the aspect of spatially displaying the baseline digital image. The displaying of the image may assist the physician in visualizing the VOI.

In another aspect, the method includes accessing a preliminary thermal ablation plan and comparing the baseline digital image to the preliminary thermal ablation plan. The plan may include expected temperature changes at each spatial location as a function of time during the thermal ablation procedure. In one embodiment, software is employed to register the baseline digital image to an image form the preliminary thermal ablation plan. This registration may be performed without the use of artificial fiducial markers by using natural structures within the VOI as fiducial markers.

In one embodiment, the comparison of the baseline digital image to the preliminary thermal ablation plan may include spatially displaying the baseline digital image along with a planned thermal distribution at a selectable point in time during the preliminary thermal ablation plan. This spatial display may include the planned thermal distribution throughout the VOI. This spatial display may include a planned coagulation necrosis target volume.

In another aspect, the method for performing thermal ablation within a VOI in a patient may include modifying the preliminary thermal ablation plan to produce a modified thermal ablation plan based, at least in part, on the comparison of the baseline digital image to the preliminary thermal ablation plan. This modification may be performed to compensate for any changes that may have occurred within the VOI between the time of the preliminary thermal ablation plan and the time of the capture of the baseline digital image. Such changes may, for example, include tumor growth or tumor shrinkage.

According to yet another aspect there is provided a method for performing thermal ablation within a VOI in a patient that includes performing thermal ablation on at least a first sub-volume of the VOI according to at least a portion of a first thermal ablation plan. In one embodiment, the thermal ablation may be performed using one or more of the following modes: RFA, laser ablation, microwave, extracorporeal focused ultrasound ablation, direct focused ultrasound ablation, and cryoablation. The thermal ablation may be performed using a plurality of different modes of thermal ablation delivery.

In another embodiment of the current aspect, one or more of the thermal ablation applicators may include features to enable a stereotactic location system to track the position of the applicator. This may be used to aid a physician in the positioning of the applicator for delivery of the thermal ablation. In another embodiment, an automated insertion system may be present operable to insert a thermal ablation applicator into a position to deliver the thermal ablation. In still another embodiment of the current aspect, the thermal ablation applicator may be guided into position using ultrasound imaging and once in position, the thermal ablation may be delivered. One or more of the thermal ablation applicators may be actively controlled through a closed-loop feedback thermal ablation delivery control system.

Applicator positioning may be attempted to be within spatial tolerances of the planned applicator position. Once positioned, the accuracy of the positioning may be verified. The verification may be performed, for example, by ultrasound or x-ray imaging, or by a stereotactic location system. If the applicator position is found to be out of plan tolerances, the plan may be modified to accommodate the actual applicator position. The plan modification may include modifying a non-positional aspect of the plan (e.g. thermal ablation applicator power level or thermal ablation delivery time). Alternatively, the applicator may be repositioned to be within plan tolerances.

In another aspect there is provided a method for performing thermal ablation within a VOI in a patient that includes performing thermal ablation on at least a first sub-volume of the VOI and periodically imaging a predetermined location within the VOI and triggering the capturing of a temperature differential digital image based at least in part on the periodic imaging. A temperature differential image is an image that contains information that may be used to determine temperature changes. For example, a temperature differential image may be compared to another image of substantially the same VOI and temperature changes may be inferred from the differences in the two images. In the case of temperature differential images generated using an x-ray system, the temperature changes may be derived from differences in the Hounsfield unit data for each spatial location captured in the images. The periodic imaging may be accomplished by one or more of the following methods: ultrasound, ultrasound with ARFI capabilities, and ultrasound with elastography capabilities. An additional aspect includes periodically measuring temperature at a predetermined location within the VOI and triggering the capturing of a temperature differential digital image based at least in part on the periodic measuring. The periodic temperature measurement may be accomplished through the use of temperature sensors attached to thermal ablation applicators or other types of temperature sensors known to those skilled in the art such as separate temperature probes situated within or around the VOI.

According to still another aspect there is provided a method for performing thermal ablation within a VOI in a patient that includes capturing a temperature differential digital image of the VOI with an x-ray system, wherein the temperature differential digital image includes a set of detected image signal data substantially corresponding with the array of spatial locations throughout the VOI. In one embodiment of the current aspect, the capturing of the temperature differential digital image includes illuminating the VOI with x-rays, detecting a plurality of portions of the x-rays that passed through the VOI and at least partially generating the temperature differential digital image based on the detected x-rays. The temperature differential digital image may include information obtained through a supplemental imaging modality. The supplemental imaging modality may utilize image enhancing software. The supplemental imaging modality may also employ visualization software to better communicate with the physician regarding the structure and features of the VOI. In addition to the information gathered from the x-ray imaging process, the temperature differential digital image may also be at least partially based on information obtained through an additional imaging modality such as ultrasound, ultrasound with ARFI capabilities, ultrasound with elastography capabilities, PET, SPECT and MRI. These additional imaging modalities may use contrast agents to assist in the capturing of image information. The capturing of the temperature differential digital image may include calibrating the temperature differential digital image. This calibration may include measuring the temperature of at least a first spatial location (corresponding to the same locations measured when calibrating the baseline digital image previously described) within the VOI and correlating the measured temperature to the temperature differential digital image at the same spatial location. This correlation between temperature differential digital image and temperature may then be combined with the correlation previously discussed between the baseline digital image and temperature to develop a mathematical relationship between the values obtained from the imaging process (e.g. Hounsfield units measured at a particular location) and actual temperature. This relationship may then be applied across the VOI to yield calibrated temperatures across the VOI.

In one embodiment of the current aspect, the temperature differential digital image may be spatially filtered. The spatial filter may be a Gaussian filter or any other filter, known to those skilled in the art, which may enhance the utility of the generated images. In an additional embodiment, the temperature differential digital image may be displayed to communicate information pertaining to the VOI to a physician.

According to yet another aspect there is provided a method for performing thermal ablation within a VOI in a patient that includes capturing a baseline digital image of the VOI, capturing a temperature differential digital image of the VOI and registering the temperature differential digital image to the baseline digital image. In one embodiment of the present aspect, the baseline digital image and the temperature differential digital image may be registered to a single external coordinate system. In another embodiment, software may be employed to register the temperature differential digital image to the baseline digital image without the use of artificial fiducial markers. In such an embodiment, the software may be able to use internal structures within the images as natural fiducial markers and register the images by aligning those natural fiducial markers.

In yet another aspect, there is provided a method for performing thermal ablation within a VOI in a patient that includes capturing a baseline digital image of the VOI, capturing a temperature differential digital image of the VOI and inferring, based at least in part on the baseline digital image and the temperature differential digital image, an amount of temperature change at substantially each spatial location within an array of spatial locations within the VOI. This is accomplished by calculating image signal data changes between the baseline digital image and the temperature differential digital image for substantially each spatial location within the array in one particular embodiment. This embodiment may further include determining Hounsfield unit changes for substantially each spatial location within the array.

One embodiment of the current aspect includes calculating a predicted coagulation necrosis volume based, at least in part, on the inferred amount of temperature change at substantially each spatial location within the array. This embodiment may further include displaying the predicted coagulation necrosis volume. This embodiment may also include comparing the predicted coagulation necrosis volume to a planned coagulation necrosis volume.

Still another embodiment of the current aspect may include displaying the temperature changes of the current aspect in the form of isothermal regions wherein each of the isothermal regions represent temperature ranges of at most 15° C. More preferably, the isothermal regions may represent temperature ranges of at most 1° C.

Yet another embodiment of the current aspect may include displaying an image of at least a portion of the VOI in which the inferred temperature changes are visually discernable. In one embodiment, this may include displaying at least a portion of the image of at least a portion of the VOI in a volume rendered three-dimensional view including shaded isothermal three-dimensional regions within the VOI. In another embodiment, this may include displaying at least a portion of the image of at least a portion of the VOI as a selectable two-dimensional slice through the VOI. In still another embodiment, this may include displaying at least a portion of the image of at least a portion of the VOI as isothermal regions in a selectable two-dimensional slice through the VOI. And in yet another embodiment, this may include displaying the inferred temperature changes relative to a display of planned temperature changes from a thermal ablation plan. In another embodiment, the display may be a Multi-Planar Reformatted display or a three-dimensional volume rendered display. The display may be in the form of a combination of two or more of the aforementioned display techniques or any other display technique known to those skilled in the art.

According to another aspect there is provided a method for performing thermal ablation within a VOI in a patient that includes comparing inferred temperature changes at substantially each spatial location within an array of spatial locations within the VOI to expected temperature changes at substantially each spatial location within the array from a first thermal ablation plan. In one embodiment, the method further includes continuing thermal ablation according to the first thermal ablation plan if the inferred temperature changes are within a predetermined range of the expected temperature changes. In another embodiment of the current aspect, the method further includes adjusting the first thermal ablation plan to create a second thermal ablation plan, wherein the adjusting is based at least in part on the comparison of the present aspect. These embodiments may further include storing the second thermal ablation plan in a memory module. The second plan may be a new plan or it may be a modified version of the first plan. With respect to the second plan being a modified version of the first plan, by way of example, any one or more of the following aspects of the first plan may be modified to create the second plan:

target coagulation necrosis volume;
    planned coagulation necrosis volume;
    thermal ablation applicator quantity;
    thermal ablation applicator type or types;
    thermal ablation applicator power level (for each applicator);
    thermal ablation applicator position (for each applicator);

thermal ablation applicator target (for each applicator);
temperature differential image triggering parameters (used to determine when a temperature differential image should be captured);
supplemental imaging modalities;
patient positioning; and
temperature differential image capture schedule.

The second plan may further contain expected temperature changes throughout the VOI as a function of time during the portion of the thermal ablation procedure conducted according to the second plan. Where thermal ablation applicator position is different in the second plan from the first plan, the adjustment of thermal ablation applicator position may be performed by a physician or robotic system. In one embodiment, the adjustment of thermal ablation parameters is at least partially performed by a closed-loop feedback control system. In another embodiment, the closed-loop feedback control system uses the inferred temperature changes as a basis for control.

According to another aspect there is provided a method for performing thermal ablation within a VOI in a patient that includes performing thermal ablation according to a first thermal ablation plan on a first sub-volume within the VOI, modifying the first thermal ablation plan during the thermal ablation to create a second thermal ablation plan and continuing thermal ablation on at least a second sub-volume within the VOI according to at least a portion of the second thermal ablation plan. In one embodiment of the current aspect, the first sub-volume is substantially the same as the second sub-volume. In an alternative to this embodiment, the first sub-volume is not substantially the same as the second sub-volume.

According to still another aspect there is provided a method for performing thermal ablation within a VOI in a patient that includes capturing a plurality of temperature differential digital images, registering the plurality of temperature differential digital images to a baseline digital image and inferring an amount of temperature change at substantially each spatial location within an array of spatial locations within the VOI relative to a previously captured digital image. In one embodiment, the previously captured image is the baseline digital image. In another embodiment, the previously captured image is a previously captured temperature differential digital image.

According to another aspect there is provided a method for performing thermal ablation within a VOI in a patient that includes performing thermal ablation on at least a first sub-volume of the VOI according to at least a portion of a first thermal ablation plan, capturing a first temperature differential digital image of the VOI, registering the first temperature differential digital image to a baseline digital image, inferring, based at least in part on the baseline digital image and the first temperature differential digital image, an amount of temperature change at substantially each spatial location within an array of spatial locations within the VOI, comparing the inferred temperature changes to expected temperature changes from the first thermal ablation plan, continuing thermal ablation on at least a second sub-volume within the VOI according to at least a portion of a second thermal ablation plan, and repeating the registering, inferring, comparing and continuing steps at least one additional time. In one embodiment of the current aspect, the repeated steps may be repeated until a coagulation necrosis goal is met.

According to another aspect there is provided a method for performing thermal ablation within a VOI in a patient that includes generating a post-procedure report describing the performed thermal ablation. In one embodiment of the present aspect, the post-procedure report is at least partially conforming to the DICOM standard.

According to still another aspect there is provided a method for performing thermal ablation within a VOI in a patient including the capturing of images of the VOI wherein the capturing includes positioning an x-ray C-arm Cone-Beam Computed Tomography (CBCT) scanner so that the VOI is within a field of view of the scanner and x-rays emanating from the scanner will intersect the VOI at a first orientation. This aspect further includes illuminating, with an x-ray source of the x-ray C-arm CBCT scanner, the VOI with a first conical beam of x-rays emanating from the scanner at a first time, detecting, with a two-dimensional x-ray detector array of the x-ray C-arm CBCT scanner, a plurality of portions of the first conical beam of x-rays that passed through the VOI during the illuminating at the first time, and generating a first x-ray image signal from the plurality of portions of x-rays of the detected first conical beam, the first x-ray image signal including x-ray image values corresponding with an array of spatial locations throughout the VOI.

In one embodiment of the current aspect, the capturing of images of the VOI further includes repositioning the scanner so that the VOI remains within the field of view of the scanner and x-rays emanating from the scanner intersect the VOI at a second orientation, illuminating the VOI with a second conical beam of x-rays emanating from the scanner at a second time, detecting, with the two-dimensional x-ray detector array, a plurality of portions of the second conical beam of x-rays that passed through the VOI during the illuminating at the second time, and generating a second x-ray image signal from the plurality of portions of x-rays of the detected second conical beam. In a further embodiment, the repositioning, detecting, and generating steps are repeated to generate additional image signals until a sufficient number of x-ray image signals have been generated to enable a three-dimensional image data set of a predetermined resolution to be created. In a further embodiment, the three-dimensional image data set may be generated from the generated image signals of the previous embodiment.

In another embodiment, the entire present aspect may be repeated a plurality of times during the performance of the method of thermal ablation to generate a plurality of temperature differential digital images during the thermal ablation. In a related embodiment, three-dimensional resultant image data sets may be generated from the comparison of two of the plurality of generated three-dimensional image data sets, wherein the three-dimensional resultant image data sets contain thermal information indicative of relative magnitudes of temperature changes between the three-dimensional image data sets.

In still another related embodiment, one of the two generated three-dimensional image data sets used in the comparison of the preceding embodiment may be the baseline digital image wherein the baseline digital image provides a static reference for generating successive resultant image data sets. In yet another related embodiment, both of the two generated three-dimensional image data sets used in the comparison may be temperature differential digital images wherein one of the two generated three-dimensional image data sets used in the comparison provides a dynamic reference for generating successive resultant image data sets. A physician may select between using a static reference or a dynamic reference for use in generating successive resultant image data sets. A physician may switch back and forth between static and dynamic references during the thermal ablation.

In yet another related embodiment, the thermal information may be displayed so that the relative magnitudes of temperature changes throughout the VOI are visually discernable.

In an additional embodiment of the current aspect, the x-ray C-arm CBCT scanner may define an access corridor that is a sector of a circle centered at the center of a C-arm and in the same plane as the C-arm. In this embodiment, the VOI may be accessed during the thermal ablation through the access corridor. In a related embodiment, the steps of positioning applicators, delivering thermal ablation and manipulating applicators may all be accomplished by accessing the VOI through the access corridor. Indeed, access to the VOI may be maintained through the access corridor throughout the entire thermal ablation procedure.

According to another aspect, there is provided a method for performing thermal ablation within a VOI in a patient wherein the patient remains substantially stationary relative to a patient bed throughout the entire thermal ablation procedure. In a related embodiment, the patient bed may not need to be moved substantially more than a maximum lineal dimension of the VOI during the entire thermal ablation procedure. For example, the only patient movement during the thermal ablation procedure may be the movement of the patient bed relative to the x-ray system during imaging. Since the purpose of the movement is to position portions of the VOI within the field of view of the scanner, the movement may need to only be about the length of the VOI in the direction of patient bed movement.

In a further related embodiment, the x-ray system may be operable to translate in the direction perpendicular to a plane defined by a vertical plane in which the x-ray source and detector may rotate. In such an embodiment, the patient may remain stationary throughout the entire thermal ablation procedure.

In a further related embodiment, the scanner may be operable to image a three-dimensional volume without translating. Such configurations include where the scanner is operable to raster a one-dimensional scan beam across a second dimension, or where the scanner is operable to produce a conical x-ray beam. Such scanners may be operable to produce a three-dimensional image of the VOI with no substantial patient movement, allowing the patient to remain stationary throughout the entire thermal ablation procedure. Combinations of the aforementioned embodiments may be used to minimize or eliminate patient movement.

According to one aspect, there is provided a method of performing a thermal ablation procedure within a VOI in a patient including the steps of capturing a baseline digital image of a VOI in a patient, performing thermal ablation on at least a first sub-volume of the VOI according to at least a portion of a first thermal ablation plan, capturing a first temperature differential digital image of the VOI, registering the first temperature differential digital image to the baseline digital image, inferring temperature changes throughout the VOI, and comparing the temperature changes to expected temperature changes from the plan. In this aspect, the capturing steps include the steps of positioning an x-ray CT scanner so that the VOI is within a field of view of the scanner, illuminating the VOI with a first beam of x-rays, detecting a plurality of portions of the first beam of x-rays that passed through said VOI during the illuminating, and generating a first x-ray image signal from the plurality of portions of x-rays, where the first x-ray image signal includes x-ray image values corresponding with an array of spatial locations throughout the VOI.

According to another aspect, the capturing of images includes repositioning the scanner so that the VOI remains within the field of view of the scanner, illuminating the VOI with a second beam of x-rays, detecting the second beam of x-rays, and generating a second x-ray image signal. In one embodiment, the steps of repositioning, illuminating, detecting and generating may be repeated a plurality of times to generate additional x-ray image signals until a sufficient number of x-ray image signals have been generated to enable a three-dimensional image data set of a predetermined resolution to be created. Three-dimensional image data sets may then be generated from the generated image signals.

In yet another aspect, the performing of thermal ablation may include positioning at least one thermal ablation applicator relative to the VOI, delivering thermal ablation via the at least one applicator, manipulating the at least one applicator; and maintaining access to the VOI through an access corridor throughout each of the inserting, delivering and manipulating steps.

According to one aspect there is provided a method for performing thermal ablation within a VOI in a patient that includes positioning a patient so that the VOI is within a field of view of an imaging device. Also in this aspect, the imaging device encircles less than all of the VOI and may be capable of illuminating the VOI with a conical beam of x-rays which may then be detected by a two-dimensional flat panel sensor array.

According to another aspect there is provided a method for performing thermal ablation within a VOI in a patient that includes capturing a baseline digital image of the VOI with the imaging device described in the discussion of the previous aspect. In one embodiment of the present aspect, the baseline digital image may be calibrated by measuring temperature of at least a first spatial location within the VOI and correlating the measured temperature to the baseline digital image at that location.

According to another aspect there is provided a method for performing thermal ablation within a VOI in a patient that includes performing thermal ablation on at least a first sub-volume of the VOI according to at least a portion of a thermal ablation plan. In one embodiment, the performing of the thermal ablation is performed using a mode selected from RFA, laser ablation, microwave, extracorporeal focused ultrasound ablation, direct focused ultrasound ablation, and cryoablation. In another embodiment, the performing of thermal ablation is done using at least two of the aforementioned modes.

According to another aspect there is provided a method for performing thermal ablation within a VOI in a patient that includes adjusting a thermal ablation plan based at least in part on differences between a baseline digital image and a temperature differential digital image. The temperature differential digital image may be calibrated by measuring temperature of at least a first spatial location (corresponding to the same locations measured when calibrating the baseline digital image previously described) within the VOI at or near the time the temperature differential is being captured and correlating the measured temperature to the temperature differential digital image at that location. This correlation between temperature differential digital image and temperature may then be combined with the correlation previously discussed between the baseline digital image and temperature to develop a mathematical relationship between the values obtained from the imaging process (e.g. Hounsfield units measured at a particular location) and actual temperature. This relationship may then be applied across the VOI to yield calibrated temperatures across the VOI.

In one embodiment of the current aspect, the adjusting the thermal ablation plan creates an adjusted thermal ablation plan, which is then stored in a memory module. In another embodiment of the current aspect, the adjusted thermal ablation plan includes adjusting at least one of thermal ablation applicator quantity, thermal ablation applicator type, thermal ablation applicator power, thermal ablation applicator delivery direction, thermal ablation applicator position, and thermal ablation applicator target point. The adjustment may be completed by a physician, automatically (e.g. by a robotic system), or by some combination thereof. The adjustment parameters may be generated by a closed-loop feedback control system. The thermal ablation method of the current aspect may be continued until a coagulation necrosis goal is achieved.

According to another aspect, once the patient is positioned, the patient position may be maintained throughout the thermal ablation procedure. Alternatively, the patient position may be maintained relative to the patient bed and the position of the patient and patient bed together may be only moved a short distance perpendicular to a transverse plane of the patient during scanning, such as the length of the VOI in the direction perpendicular to the plane defined by a vertical plane in which the x-ray source and detector may rotate.

According to one aspect, there is provided a method of inferring thermal changes within a VOI in a patient occurring during thermal ablation that includes capturing a baseline image with an x-ray system, performing thermal ablation, capturing a temperature differential image with the x-ray system, registering the temperature differential image to the baseline image, calculating image signal data changes for substantially each voxel within the VOI, and inferring temperature changes for substantially each voxel. According to this aspect, the baseline digital image of the VOI in the patient is made up of detected image signal data corresponding with a baseline array of spatial locations substantially throughout the VOI. In this aspect, each voxel represents a volume of at most 1 $cm^3$. Furthermore, in this aspect the patient position may be maintained throughout the thermal ablation procedure.

In one embodiment of the present aspect, the image capturing of the baseline digital image and the first temperature differential digital image are performed at least in part by an x-ray CT scanner. Furthermore, the x-ray CT scanner may be an x-ray CBCT scanner. Another embodiment of the present aspect includes displaying an image before the physician in which the inferred temperature changes are visually discernible. This display may, for example, take the form of a display of the VOI with an overlay of isothermal lines or regions representing temperatures within the VOI. The display may also include shaded isothermal three-dimensional volumes or isothermal lines or isothermal regions superimposed on an image of a two-dimensional slice of the VOI, or any combination of three-dimensional and two-dimensional representations. In one embodiment each voxel represents a volume of at most 1 $mm^3$.

According to one aspect, there is provided a method of predicting a coagulation necrosis volume caused by thermal ablation performed during a thermal ablation procedure that includes capturing a baseline digital image of a VOI in a patient with an x-ray system, performing thermal ablation, capturing a first temperature differential digital image of the VOI with the x-ray system, registering the first temperature differential digital image to the baseline digital image, calculating image signal data changes for substantially each spatial location within the first temperature differential, inferring temperature changes based on the calculating step, and predicting a coagulation necrosis volume based on time-temperature integration caused by the thermal ablation up to a user selected point in time where the time-temperature integration is based on the inferred temperature changes. The method may include displaying the predicted coagulation necrosis volume. The display may include displaying the predicted coagulation necrosis volume along with a planned coagulation necrosis volume from a thermal ablation plan.

In one embodiment of the present aspect, the capturing of the baseline digital image and the first temperature differential digital image are performed at least in part by an x-ray CBCT scanner. The display may comprise different colored regions where each different color corresponds to a different inferred temperature within the VOI.

Additional aspects and advantages of the present invention will become apparent to one skilled in the art upon consideration of the further description that follows. It should be understood that the detailed description and specific examples are intended for purposes of illustration only and are not intended to limit the scope of the invention.

BRIEF DESCRIPTION OF THE DRAWINGS

For a more complete understanding of the present invention and further advantages thereof, reference is now made to the following Detailed Description of the Invention taken in conjunction with the accompanying drawings, wherein:

FIG. 9 is a flowchart for a method of performing thermal ablation within a VOI in a patient in accordance with another embodiment of the present invention.

FIG. 10 is a flowchart for a method of inferring thermal changes within a VOI occurring during thermal ablation.

FIG. 11 is a flowchart for a method of predicting a coagulation necrosis volume caused by a thermal ablation procedure.

DETAILED DESCRIPTION OF THE INVENTION

In the following description, the invention is set forth in the context of apparatus and methods for planning, simulating and performing thermal ablation in a patient.

Figure 1:
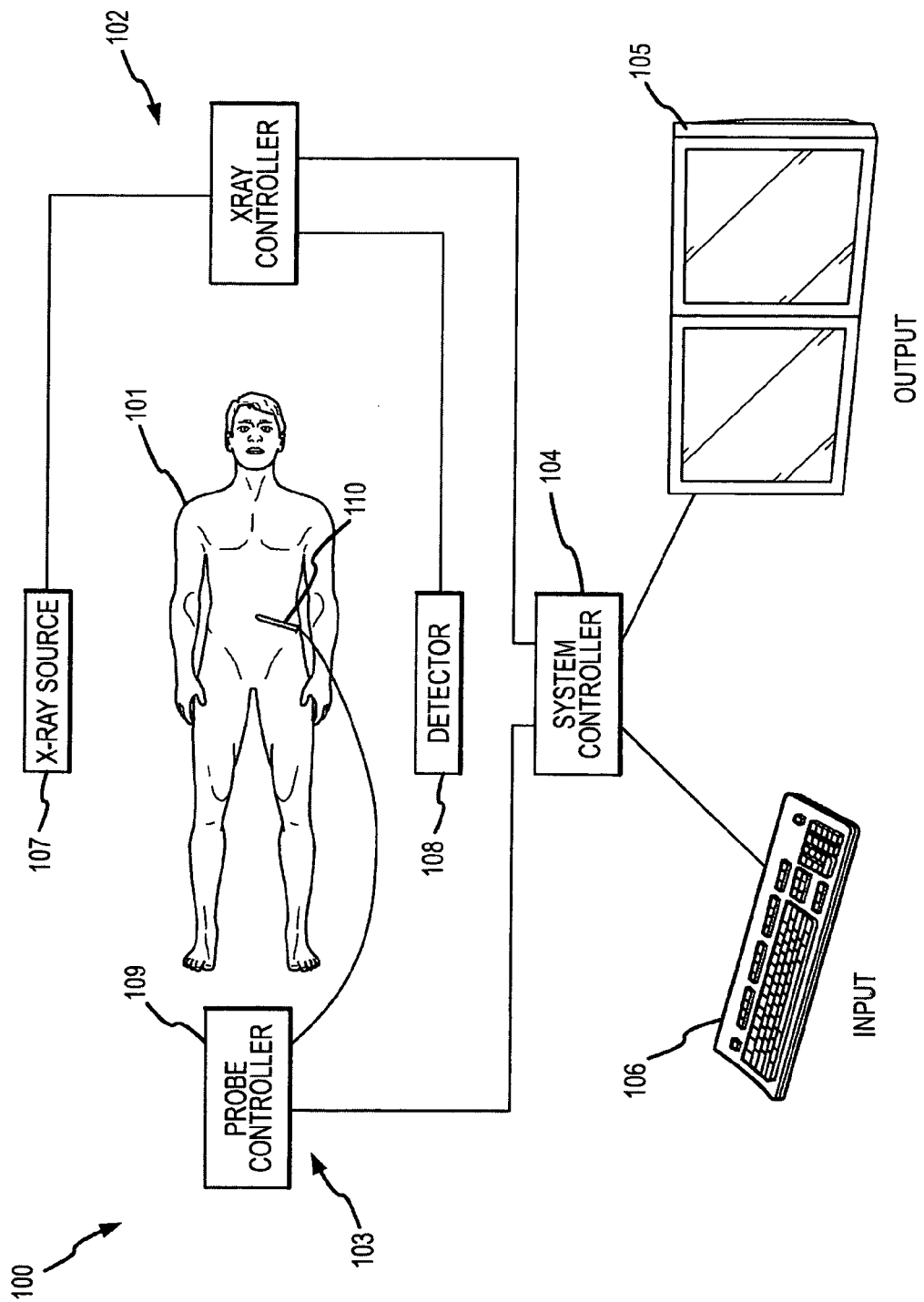
FIG. 1 is a schematic diagram of a system for performing thermal ablation in accordance with an embodiment of the present invention.

FIG. 1 illustrates, in schematic form, a thermal ablation apparatus 100 for performing thermal ablation on a patient 101. The illustrated components, each of which will be described in detail, are an x-ray imaging system 102, a thermal ablation delivery system 103 and a system controller 104. Interfaces for the thermal ablation apparatus 100 are represented schematically by an output device 105 and an input device 106.

The thermal ablation apparatus 100 is capable of performing a thermal ablation procedure within a Volume Of Interest (VOI) within a patient 101. During the procedure, the x-ray imaging system 102 may capture images of the VOI which may then be used by the system controller 104 to control the thermal ablation delivery system 103 to achieve the goals of a thermal ablation plan. The primary goal of the thermal ablation plan may be to produce coagulation necrosis in a targeted area or areas, such as a cancerous tumor, contained within the VOI. By way of example, the thermal ablation plan may include any one or more of the following:

expected temperature changes throughout the VOI as a function of time during the thermal ablation procedure;
thermal ablation applicator quantity;
thermal ablation applicator type or types;
thermal ablation applicator power level (for each applicator);
thermal ablation applicator position (for each applicator);
thermal ablation applicator target (for each applicator);
temperature differential image triggering parameters;
supplemental imaging modalities;
patient positioning; and
temperature differential image capture schedule.

The x-ray imaging system 102 may be an x-ray Computed Tomography (CT) scanner operable to measure temperature changes across a VOI in a patient 101. Generally, x-ray imaging systems measure the radiodensity of objects within their field of view. The radiodensity may be determined in terms of Hounsfield Units (HUs). In the thermal ablation apparatus 100, the x-ray imaging system 102 may comprise an x-ray source 107 and a detector 108. The x-ray source 107 will be operable to emit x-ray energy in the direction of the detector 108. Objects, such as the patient 101, between the x-ray source 107 and the detector 108 are said to be in the field of view of the x-ray imaging system 102.

Various materials will absorb x-ray energy at different rates. Bone, for example, will absorb more x-ray energy than muscle tissue. Traditional film based x-ray imaging systems exploit this variation to produce two-dimensional images of bone and other tissue structures within a patient. The difference between the radiodensity of bone and muscle is relatively large and therefore high contrast images may be produced. Radiodensity can also vary with temperature. For example, the radiodensity of water will change as a function of temperature for a given pressure. Compared to the difference between bone and muscle, the changes are relatively small. However, the changes are detectable. Since human tissue is largely made up of water, it too will experience changes in radiodensity as a function of temperature. Measuring this phenomenon is the basis for the ability of the x-ray imaging system 102 to detect temperature changes within the VOI of the patient 101.

The x-ray imaging system 102 may be a CT scanner capable of producing rendered three-dimensional views of a VOI within a patient 101 within the field of view of the scanner. In one embodiment, the x-ray imaging system 102 is capable of producing three-dimensional views where the voxels, or volume elements of the image, may be no larger than 1.0 mm$^3$. And in an alternate embodiment, the voxels of the three-dimensional views may be no larger than 0.35 mm$^3$.

Figure 2:
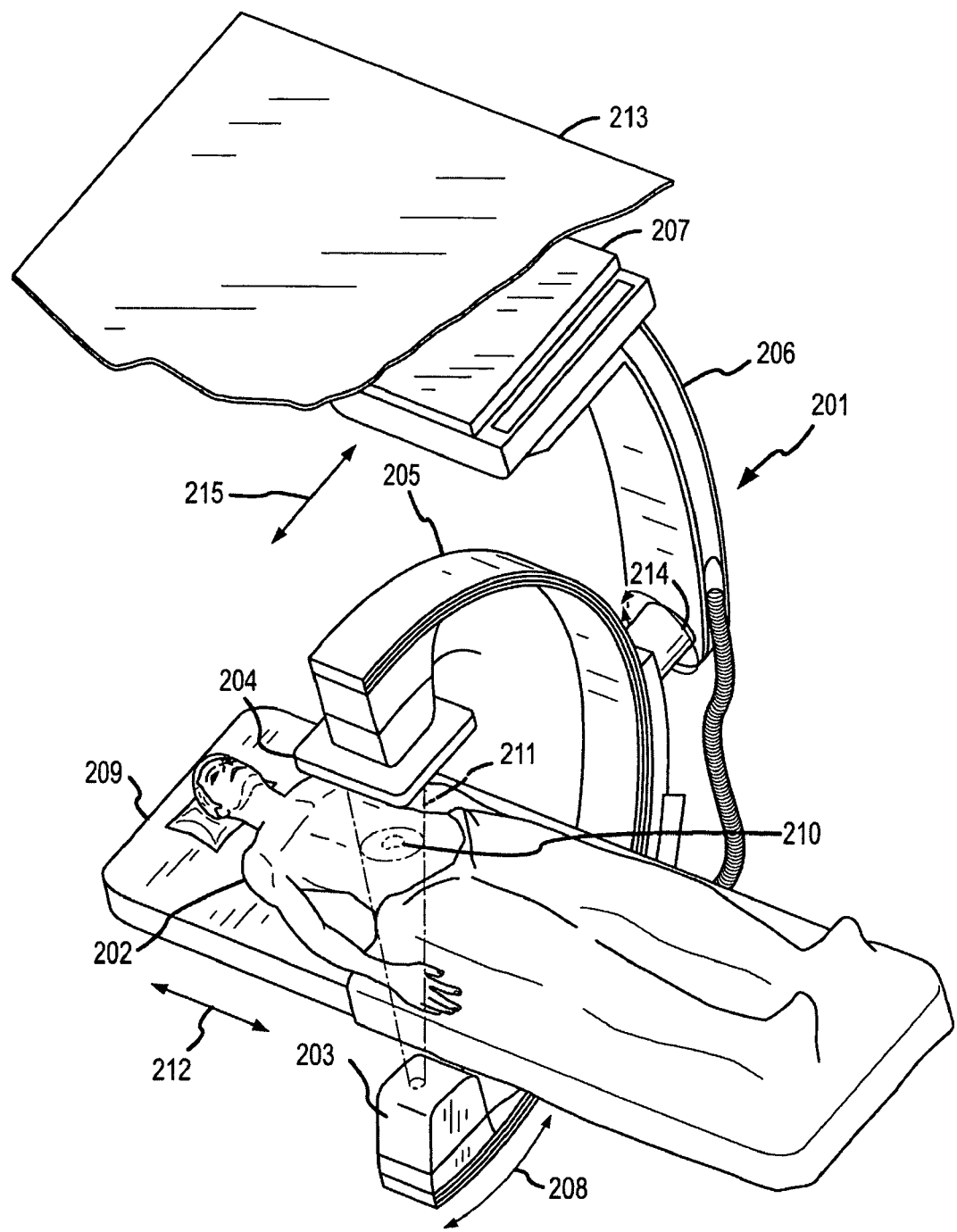
FIG. 2 is a perspective view of a C-arm x-ray CT scanner in accordance with an embodiment of the present invention.

The x-ray imaging system 102 may be in the form of a C-arm x-ray imaging system 201 as illustrated in FIG. 2. The C-arm configuration, as opposed to a traditional closed configuration, provides greater access to the patient 202. X-ray CT scanners with a traditional closed configuration use a ring or doughnut to house the x-ray source and detector. The patient must be moved through the ring in order to obtain an image. The ring may limit access to the patient during the imaging process. In contrast, a C-arm x-ray imaging system 201 may allow access to the patient even during the imaging process. This access may be through an access corridor defined by the C-arm x-ray imaging system. The access corridor may be a sector of a circle centered at the center of the C-arm and in the same plane as the C-arm in which the C-arm does not enter as it moves during the imaging process. Therefore, apparatuses, for example cables attached to applicators or sensors, may pass through the access corridor to the VOI and remain attached during the imaging process.

In FIG. 2, the C-arm x-ray CT scanner 201 comprises an x-ray source 203 and a detector 204 connected by a C-arm 205. The C-arm 205 is connected to the base 207 by a support arm 206. As illustrated in FIG. 2, the base 207 may be mounted to the ceiling along a structure that enables the entire C-arm 205 to be moved in and out of an imaging position along a movement axis 215. In this manner, the C-arm 205 may be moved away from the patient 202 when it is not actively imaging the patient 202. Alternatively, the C-arm 205 may remain in proximity to the patient 202 during the entire thermal ablation procedure, thus reducing imaging cycle times and simplifying image registration. The C-arm 205 may move relative to the support arm 206 so that it rotates about the center of the "C" as shown by directional indicator 208. The C-arm 205 may also be operable to rotate about an axis parallel to the support arm 206. The patient bed 209 may also be operable to translate relative to the C-arm 205 as shown by directional indicator 212. The patient bed 209 may not need to be moved substantially more than a maximum lineal dimension of the VOI. In other words, during the entire thermal ablation procedure, the only patient 202 movement that may be required is to translate the patient 202 and the patient bed 209 in the direction shown by the directional indicator 212 during imaging, and that the distance moved may not need to be longer than the length of the VOI along the axis 212 of patient bed movement. This minimal amount of patient movement, along with access afforded by the C-arm design may allow physician and instrument access to be maintained uninterrupted throughout the entire thermal ablation procedure. Moreover, the C-arm 205 may be operable to translate relative to the patient bed 209 in the same direction as shown by directional indicator 212 thereby eliminating all need to move the patient 202 during the entire thermal ablation procedure. The flexibility of movement of the C-arm 205 also results in the ability of a VOI 210 within the patient 202 to be imaged from a plurality of angles and C-arm 205 positions.

Figure 3:
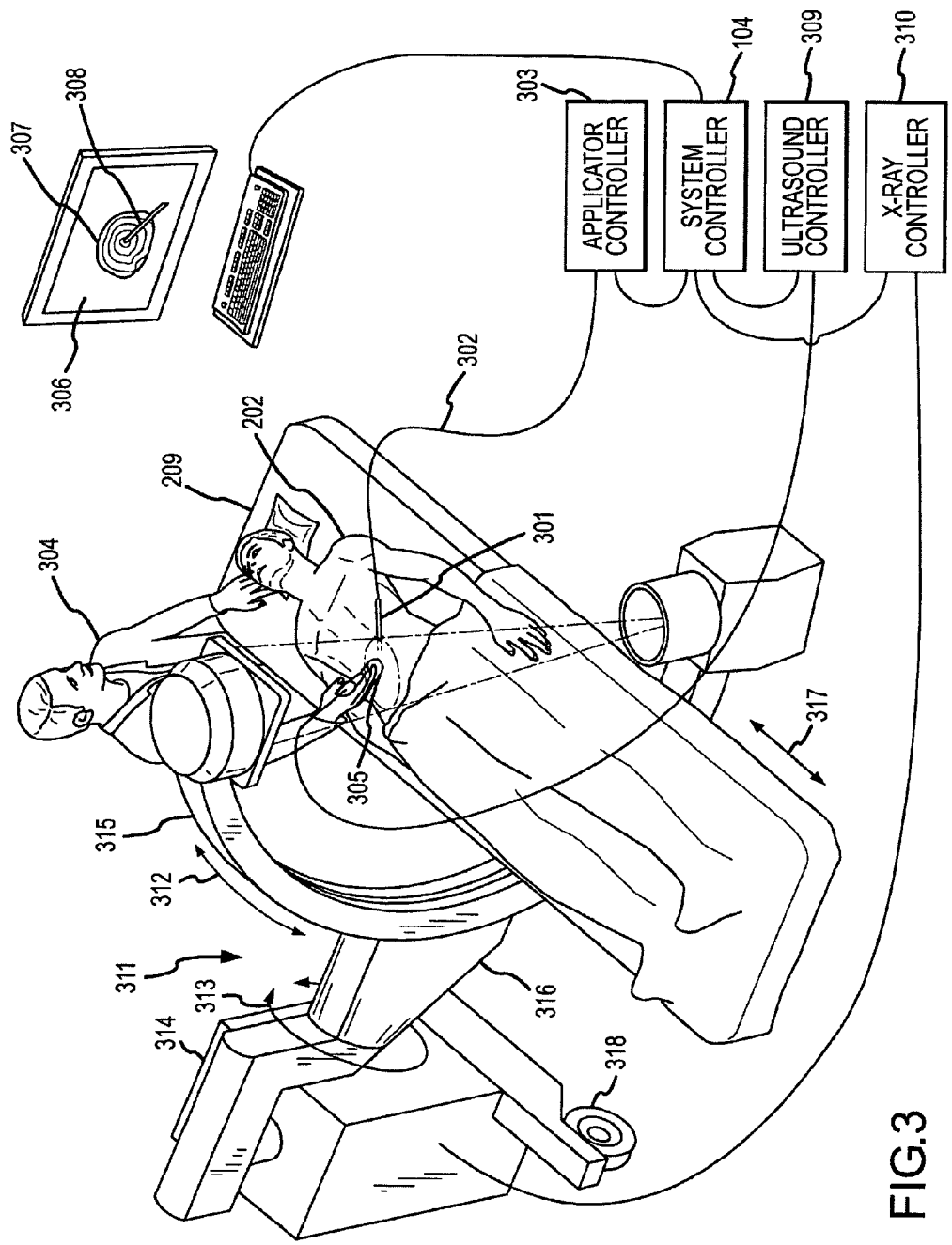
FIG. 3 is a perspective view of a thermal ablation procedure being performed on a patient in accordance with an embodiment of the present invention.

The aforementioned features may allow thermal ablation applicators and related equipment to remain in place within and around the patient 202 during the imaging process or throughout the entire thermal ablation procedure. This is illustrated in FIG. 3, which depicts a thermal ablation procedure in progress. As shown in FIG. 3, the base 314 of the C-arm x-ray CT scanner 311 may be mobile and operable to be wheeled or moved into an imaging position. Alternatively, the C-arm x-ray CT scanner 311 may be fixedly mounted to the floor or in any other manner known to those skilled in the art. Similar to the C-arm 205 depicted in FIG. 2, the C-arm 315 shown in FIG. 3 may move in a variety of ways. The C-arm 315 may move relative to the support arm 316 so that it rotates about the center of the "C" as shown by directional indicator 312. The C-arm 315 may also be operable to rotate 313 about an axis parallel to the support arm 316. The patient bed 209 may also be operable to translate relative to the C-arm 315 as shown by directional indicator 317. Moreover, the C-arm 315 may be operable to translate relative to the patient bed 209 in the same direction as shown by directional indicator 317.

The C-arm x-ray CT scanners disclosed herein may be fixed or mobile. In FIG. 2, the C-arm x-ray CT scanner 201 is fixed in that it is rigidly attached to a base 207 which is attached to the ceiling 213. The fixed C-arm x-ray CT scanner 201 may be attached to the ceiling as shown or to the floor or any other permanent structure. In FIG. 3, the C-arm x-ray CT scanner 311 is mobile in that it is not rigidly attached to any structure. The illustrated C-arm x-ray CT scanner 311 is mounted on wheels and may be moved freely throughout the procedure area.

Earlier generations of x-ray CT scanners utilized a doughnut shaped enclosure to house the x-ray source and detector. The x-ray source and detector would rotate about the VOI to produce a two-dimensional slice of the VOI. The patient would then be moved relative to the doughnut and an additional image slice would be generated. Slices may then be aggregated to produce a rendered three-dimensional view of the VOI. Later generations of x-ray CT scanners, often called helical CT scanners, would move the patient through the doughnut simultaneously with the imaging process producing a helical scan. The helical scan may then be used to generate a rendered three-dimensional view of the VOI. A C-arm x-ray CT scanner 201 such as shown in FIG. 2, may be capable of generating rendered three-dimensional views of the VOI 210 utilizing circular or helical scans. The C-arm x-ray CT scanner 201 may also be operable to generate images using other scan paths, including paths in which the x-ray source 203 and detector 204 are rotated about an axis 214 perpendicular to the patient 202, paths 212 in which the patient bed is moved, and 215 in which the x-ray source 203 and detector 204 are moved. Also, images may be generated using any combination of any of the aforementioned paths.

The present invention may utilize novel scan paths to create images of the VOI. The scan paths may be designed to avoid interference with devices, such as thermal ablation applicators or monitoring equipment, in proximity to or within the patient. The scan paths may also be designed to reduce scanning times, minimize overall exposure to x-rays and/or to minimize exposure to a particular portion of the patient.

Scan resolution and scanning speed are related in that longer scan times of a particular VOI may result in improved resolution images. Therefore, image resolution may be varied to reduce scan times and/or reduce x-ray exposure. For example, a baseline image may be generated at a high resolution, whereas later images, which, for example, may be used to determine temperature changes within the VOI, may be generated at a lower resolution. Therefore, scan resolution may be dependent on the required resolution for a particular situation. For example, intermediate temperature differential images may not need to be at as high a resolution as the baseline image. Also, it may be desired to have a higher resolution temperature differential image to record peak temperatures during a thermal ablation procedure or to closely monitor the temperature of or around a critical structure within the VOI.

The C-arm x-ray CT scanners disclosed herein may also have angiographic capabilities in that the scanners may be operable to capture images of blood vessels. This imaging may be enhanced through the use of a contrast medium introduced into the patient 202.

The patient 202 of FIG. 3 has had a thermal ablation applicator 301 inserted into his mid section. A control cable 302 extends from the applicator 301 to an applicator controller 303. As can be appreciated, the C-arm 315 may rotate and/or translate and the bed 209 may translate without interfering with either the applicator 301 or the control cable 302. Additionally, a physician 304 may also have greater access to the patient 202 due to the C-arm 315 configuration. In addition, since the applicators can remain in place during the imaging process, the applicators may be operable to perform thermal ablation while the VOI is being imaged. The patient 202 may remain stationary throughout the entire thermal ablation procedure including pre and post thermal ablation imaging. The patient 202 may remain stationary relative to the patient bed 209 throughout the entire thermal ablation procedure including pre and post thermal ablation imaging.

Earlier generations of x-ray CT scanners typically produced a narrow beam of x-rays between the x-ray source and detector. These narrow beams of x-rays were detected several times at different angles as the x-ray source and detector were rotated about the VOI of the patient. The results of the detection of these individual beams of x-rays is aggregated in the CT process by methods known to those skilled in the art, to produce a two-dimensional slice of the VOI. Adjoining two-dimensional slices may then be imaged and combined to produce rendered three-dimensional views of a VOI.

Current x-ray CT scanners often utilize fan shaped beams of x-rays to generate CT images. The fan shaped beams may be detected by a one-dimensional array of x-ray detectors (i.e. a single row of detectors). Although it is computationally more complex to produce a two-dimensional image from a fan shaped beam and one-dimensional detector, the system has the advantage of producing more information per x-ray emission and detection cycle leading to shorter scan times and potentially lower x-ray radiation doses. An x-ray CT scanner utilizing a fan shaped beam may also incorporate a two-dimensional detector array. In this configuration, the fan beam may be rastered across the array to acquire a series of one-dimensional image data sets, which can then be aggregated to produce a two-dimensional image data set. By incorporated image data sets captured with the x-ray source and detector in varying orientations, three-dimensional data sets may be created which may be used to generate rendered three-dimensional views of the VOI.

It is intended that the present invention include the use of any known or yet to be developed x-ray imaging system. This may include, but not be limited to, x-ray imaging systems that use narrow beams of x-rays, fan shaped beams of x-rays, cone shaped beams (discussed below), or any other shape of x-ray beam. Other shapes of x-ray beams may include dynamically shaped x-ray beams where the beams are shaped to target specific areas of the VOI without irradiating (or minimizing exposure to) other areas of the VOI. In a similar manner, the x-ray detector used in the x-ray CT scanner may be a single point detector, a one-dimensional array of detectors or a two-dimensional array of detectors. The two-dimensional detector may be a multi-slice detector or it may be a flat panel detector. The term flat panel detector is intended to included truly flat panels, panels curved so that each detecting element in the detector is equidistant from the x-ray source and flexible panels.

Although for exemplary purposes the present invention is generally discussed and illustrated in connection with C-arm x-ray CT scanners, it is intended that the present invention include the use of other configurations of x-ray CT scanners. Theses other configurations include, but should not be limited to, traditional doughnut type x-ray CT scanners (with one or more x-ray sources and one or more detectors) and O-arm x-ray CT scanners. O-arm x-ray CT scanners have a C-shaped section wherein the scanner may be moved into position by virtue of the opening in the "C" and then a section is moved into place to form an "O" around the patient, wherein the x-ray source and detector (or sources and detectors) may then be rotated about the patient within the "O."

As shown in FIG. 2, an embodiment may utilize a cone shaped beam 211 to illuminate the VOI 210. This embodiment may also include a two-dimensional detector array in the detector 204. A cone shaped beam 211 may be operable to image a two-dimensional area with each emission and detection cycle leading to even shorter scan times and even lower x-ray radiation doses when imaging the VOI 210 as compared to point to point or fan beam imaging systems. High scan speeds and low radiation doses are beneficial features of the systems and methods disclosed herein where the generated rendered three-dimensional views of the VOI may be used in a closed-loop feedback to control the thermal ablation delivery system 103. Additionally, the shape of the beam used to illuminate the VOI 210 may be dynamically modified by multi-leaf collimaters. By dynamically shaping the x-ray beams, x-ray dosages may be minimized.

In addition to using an x-ray CT scanner to generate temperature differential images of the VOI, the x-ray CT scanner may also be operable to be used as a two-dimensional fluoroscope. In the case of scanners utilizing cone beams or rastering fan beams with two-dimensional detector arrays or flat panel detector arrays, the scanner may be operable to capture and display real-time two-dimensional images of the VOI. Also, the scanner may be operable to present a series of two-dimensional images from varying angles to give the physician a perception of the VOI in three-dimensions similar to a rotational angio C-arm scanner. These capabilities may assist the physician in visualizing the VOI for tasks such as applicator placement.

The x-ray imaging system 102, as discussed above, may be operable to measure radiodensity or HU properties of a VOI 210 within a patient 202. This ability may then be used to determine temperature changes within the VOI 210 that may take place during a thermal ablation procedure. This may be accomplished by first generating a baseline data set with the x-ray imaging system 102. The baseline data set may be a three-dimensional data set wherein each data point is a voxel and represents a unit of volume within the VOI 210. A HU measurement value may be associated with each voxel in the baseline data set. After a portion of the thermal ablation procedure has been performed, a second three-dimensional data set may be generated by the x-ray imaging system 102. As in the baseline data set, each voxel in the second three-dimensional data set may have an associated HU measurement value. The two images may then be registered (registration is discussed below) to each other and each voxel of the baseline data set may be compared to each corresponding voxel of the second data set. The differences in measured HU may be due to the temperature changes induced by the thermal ablation procedure. These data sets may be filtered prior to comparing in order to improve the signal to noise ratio. The filter may, for example, be a Gaussian filter wherein each voxel is averaged with a number of surrounding voxels. The resulting difference image data set may have a spatial resolution or voxel size of about 1 cm$^3$ or smaller. This level of resolution may be adequate to determine if a particular target coagulation necrosis volume has been subjected to enough of a temperature change over a long enough period of time to eventually result in the death of the targeted cells. However, as discussed above, the spatial resolution of the CT scanner may be as good as 0.35 mm$^3$ or smaller. Therefore, one embodiment of the present invention may be capable of generating a three-dimensional image data set representative of temperature changes throughout the VOI with a voxel size of 1 mm$^3$ or smaller.

Figure 6A:
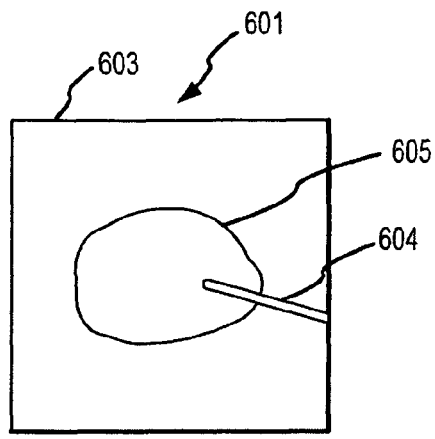
FIGS. 6A through 6F are illustrations of images generated by an embodiment of the present invention depicting the progression of isothermal regions during a thermal ablation procedure within the VOI.
Figure 6D:
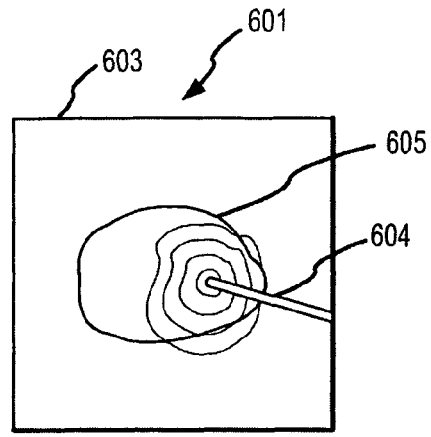
Figure 6B:
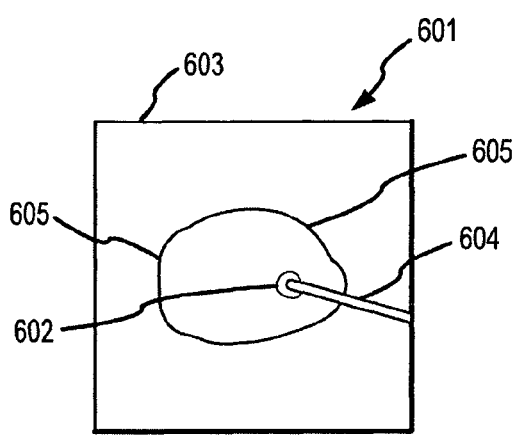
Figure 6E:
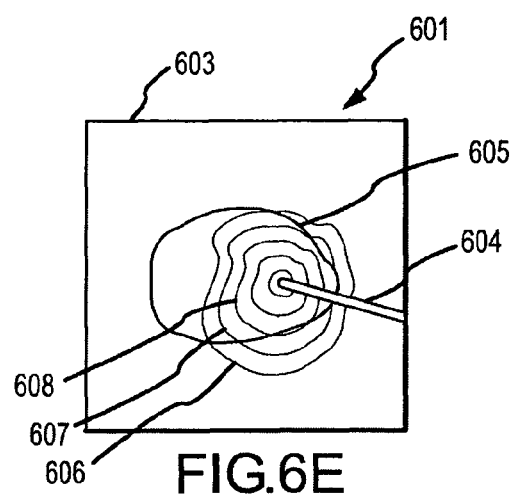
Figure 6C:
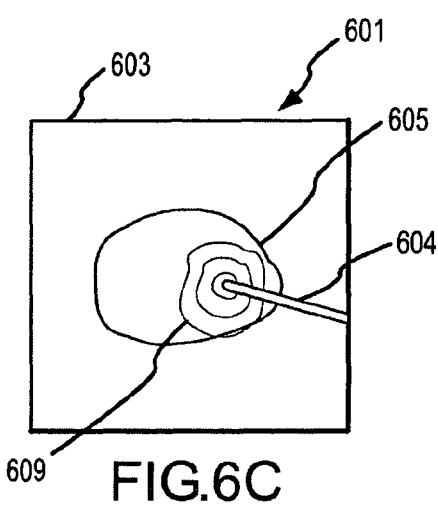

The resulting difference image data set may be displayed in a variety of ways to communicate temperature changes to the physician 304. For example, as shown in FIG. 6E, a two-dimensional image, or thermal map, may be generated comprising a two-dimensional slice 603 through the VOI 601 and multiple demarcated regions 606, 607 and 608 of elevated temperature. Each region 606, 607 and 608 may indicate a different range of temperatures. The position of the two-dimensional slice 603 relative to the VOI 601 may be physician selected. The demarcated regions 606, 607 and 608 may be indicated by a colored mask or overlay over the VOI 601 wherein the color of the mask indicates the temperature range of each demarcated region 606, 607 and 608. Other methods of indicating a temperature difference known to those skilled in the art may also be used.

The indication of temperature may be an absolute indication or a relative indication. In the case of an absolute indication of temperature, the demarcated regions 606, 607 and 608 may represent the measured temperature of the region. For example, prior to the application of thermal ablation, the entire VOI 601 may be at a relatively even temperature of 37° C. This is illustrated in FIG. 6A where no isothermal regions or bands are shown. After the application of thermal ablation, a region 602, as shown in FIG. 6B, may be at an elevated temperature of, for example, 45° C. As such, a legend may be provided in the display of FIG. 6B indicating that the color of the overlay for the demarcated region 602 is representative of the temperature of 45° C. Alternatively, the indication of temperature may be a relative indication in which case the legend provided in the display of FIG. 6B may indicate that the color of the overlay for the demarcated region 602 is representative of an 8° C. elevation over the baseline digital image temperature (in this example 37° C.).

To achieve these results, the HU data may be calibrated. This may be accomplished by, for example, using temperature calibration devices, e.g. thermocouples, mounted to the thermal ablation applicator 604 to measure the temperature at a point within the VOI 601. Prior to the application of any thermal ablation, the temperature calibration devices may be used to measure the temperature at points within the VOI 601 and these measurement points can then be correlated to the HU measurements made by the x-ray imaging system 102. During application of thermal ablation and subsequent imaging, the temperature calibration devices may continue to measure temperatures within the VOI 601 and these measurements may be correlated to subsequent HU measurements made by the x-ray imaging system 102. This correlation factor may then be applied across the VOI 601 to infer the temperature (absolute or relative) at all points throughout the VOI 601.

Figure 8A:
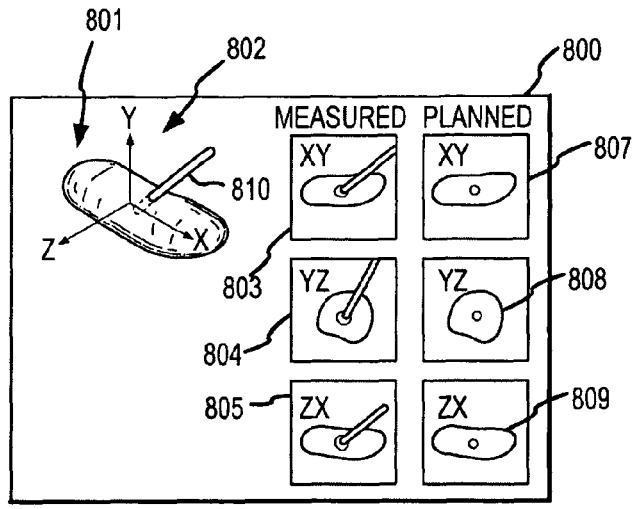
FIGS. 8A through 8C are illustrations of Multi-Planar Reformatted (MPR) display generated by an embodiment of the present invention during a thermal ablation procedure.
Figure 8B:
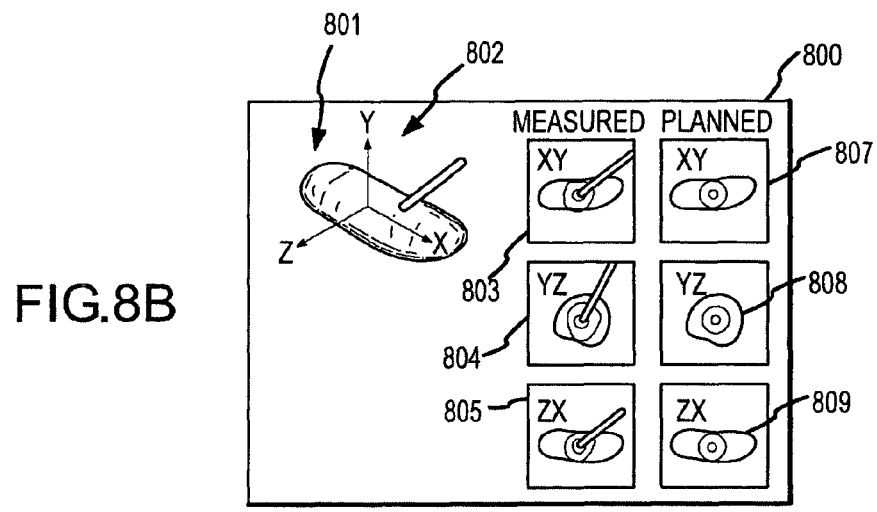
Figure 8C:
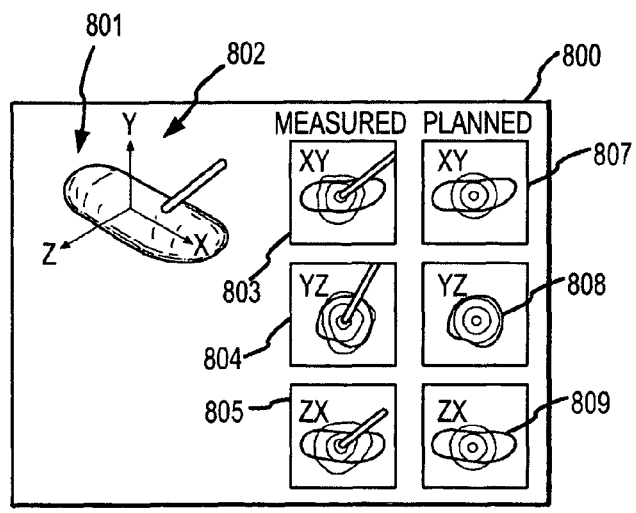

In a similar fashion, the resulting difference image set may be displayed in three spatial dimensions. FIG. 8 illustrates an embodiment of a display 800 in which a VOI 801 is illustrated in three dimensions. The display 800 may be a computer monitor. As illustrated, the VOI 801 may be shown in perspective view 802 relative to three orthogonal axes. The VOI 801 may also be shown in three dimensions by showing two-dimensional slices of three orthogonal planes 803, 804, 805 cutting through the VOI 801. Additionally, the display may incorporate time elements. In this regard, multiple resulting difference image sets may be generated and shown in sequence to communicate temperature change throughout the VOI 801 as a function of time. This is illustrated in FIGS. 6A through 6E and FIGS. 8A through 8C, which depict the propagation of temperature change throughout a VOI as a result of the application of thermal ablation emanating from the thermal ablation applicators 604 and 810.

As noted above, subsequently generated image data sets may be registered to the baseline digital image data set so that voxel by voxel comparisons may be made. This registration may be accomplished through the use of the artificial fiducial markers. These fiducial markers may be placed either internal or external to the patient 202. External fiducials may be placed on the skin of the patient 202. The fiducials may be locatable by the x-ray imaging system and serve as landmarks within the images to assist in the alignment of images to other images. Software may then be used to align the fiducials in the separate images to and therefore align the images. The registration between image data sets may also be accomplished without artificial fiducials through software. Such software may recognize natural structures within the image data sets and align and orient the structures to register the images (in effect using the natural structures as natural fiducial markers). The structure used may, for example, be the vascular structure within the VOI. The system controller 104 may comprise a registration module or subsystem for performing the registration tasks.

Returning to FIG. 3, the thermal ablation applicator 301 may be any device capable of affecting a temperature change within a VOI of a patient 202. As illustrated, the system may perform the thermal ablation procedure with a single thermal ablation applicator 301. Alternatively, multiple thermal ablation applicators may be used. The thermal ablation apparatus may include a plurality of different types of thermal ablation applicators and may also include multiple thermal ablation applicators of each different type. The thermal ablation applicators may be interstitial or extracorporeal. Among the types of thermal ablation applicators that may be included in the apparatus are Radio Frequency Ablation (RFA) electrodes, laser ablation fibers, microwave antennas, focused ultrasound transducers, and cryoprobes.

The heating effects of RFA are determined mostly by the electrical conductivity properties of the tissues being subjected to the therapy. Laser ablation heating effects are mostly determined by photon absorption and diffusion in the tissue. Microwave heating effects are a function of the dielectric properties of the targeted tissue. Focused ultrasound heating effects are determined by mechanical coupling of the ultrasonic energy into the tissues. Cryoablation uses cold applicators delivered interstitially to cause coagulation necrosis through a temperature reducing process. Each of the above types of applicators may produce different temperature change effects in different tissues resulting in differing coagulation necrosis volumes. The thermal ablation apparatus 100 may be operable to control a plurality of applicators of a plurality of different types of applicators to achieve effective coagulation necrosis of the targeted volume while keeping coagulation necrosis of the non-targeted volume to a minimum.

The system controller 104 may be operable to compare a difference image data set containing information as to temperature changes during thermal ablation, described above, to the expected temperature changes described in a thermal ablation plan. The thermal ablation plan may have been generated prior to the thermal ablation procedure and stored within the system controller 104. This comparison of temperature changes may be across the VOI. The system controller may also be operable to adjust, based on that comparison, at least one characteristic of a thermal ablation applicator. The applicator controller 109 of the thermal ablation delivery system 103 may be operable to control all of the system applicators in a closed-loop fashion. For example, the applicators may contain temperature calibration devices, such as thermocouples, or feedback mechanisms to measure the amount of energy being transmitted into (or out of in the case of a cryoprobe) the VOI. Data may be available from the device such as power, impedance, and temperature at specific areas of the device, e.g. at the tip of the deployable tines, for interstitial delivery modes. This feedback may be fed back to the applicator controller 109 to enable a closed-loop control of the applicators. In a similar fashion, the system controller 104 may control the system applicators through a closed-loop control system consisting of the x-ray imaging system 102, the system controller 104 and the applicator controller 109. In this regard, the system controller 104 may adjust the energy transmission targets of an applicator controller 109 based on the results of images generated by the x-ray imaging system 102. Also in this regard, the system controller 104 may be operable to command the x-ray imaging system 102 to generate new images of the VOI to enable the control of the applicator controller 109 and subsequently the system applicators. The commands to generate new images of the VOI may be based on, for example, the passage of a specific amount of time, an imaging schedule as per the thermal ablation plan, results of previous image generations, or applicator feedback.

The applicator controller 109 may be operable to control applicator power. Generally, this may be through a feedback loop wherein the system controller 104 instructs the applicator controller 109 to maintain or produce a specific temperature at the applicator. The applicator controller 109 may be able to use feedback mechanisms in the attached applicators to produce the targeted specific temperature profiles. Applicator power may also be controlled by the system controller 104. In this regard, the system controller 104 may instruct the applicator controller 109 to change its power delivery based on results from the x-ray imaging system 102. Other characteristics may be controlled by the system controller 104. These include sensor feedback to allow positioning of the applicator or devices, image-derived positioning of the applicator or devices, the types of applicators used, and the quantities of applicators used. For example, if a RFA applicator was not producing the expected results, the system controller 104 may determine that the RFA applicator should be replaced with a laser ablation applicator. Generally, the repositioning of applicators, the changing of the types of applicators, or the addition or removal of applicators will be performed by the physician 304 at the suggestion of the system controller 104. However, at least one of the applicators may be mounted on a robotic arm. Applicators so mounted may be inserted, repositioned, or removed automatically.

To aid the physician 304 in the placement of applicators, the thermal ablation apparatus may include an ultrasonic imaging device. As shown in FIG. 3, the ultrasound device may include a handheld transducer 305 which may be used by the physician 304 to assist in proper applicator 301 placement. An image 306 may be presented to the physician 304 showing the applicator position 308 relative to the VOI 307. The image 306 may be a real-time ultrasound image or may be an image generated by the system controller 104 overlaid with a representation of the applicator position 308.

The ultrasound system may be capable of operating in an Acoustic Radiation Force Impulse (ARFI) and/or elastography mode, which may be capable of indicating changes in the mechanical properties of tissue. The detection of changes to mechanical properties by an ARFI and/or elastography capable system may be used by the system controller 104 to aid in determination of when to generate an x-ray CT image data set. For example, the application of heat by a laser ablation fiber may cause a volume of tissue to coagulate. This coagulation may be accompanied by changes to the mechanical properties of the coagulated volume that may be detected by an ARFI and/or elestography capable system. This detected change may then be fed into the system controller 104 which may, based on this information, cause an x-ray CT image data set to be generated to determine the temperature profile of the volume. Other mechanical changes such as charring or percolation may also be detected by an ARFI and/or elestography capable system and be the basis for the system controller 104 to cause an x-ray CT image data set to be generated.

Figure 4:
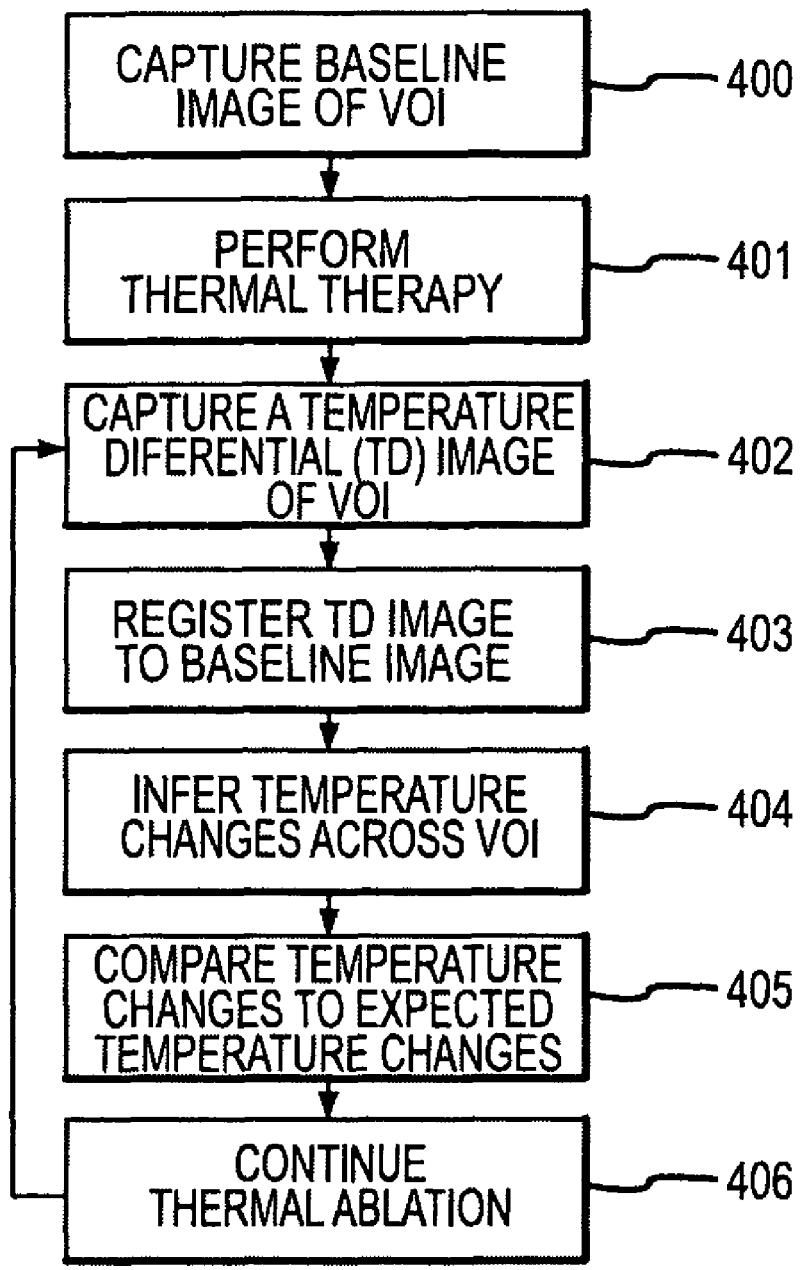
FIG. 4 is a flowchart for a method of performing thermal ablation within a VOI in a patient in accordance with another embodiment of the present invention.

FIG. 4 is a flowchart of a method of performing thermal ablation within a VOI in a patient. The first step of the method is to capture 400 a baseline digital image of a VOI in a patient with an x-ray system. Typically, the VOI will be a volume within a patient which will contain a sub-volume that is a tumor, lesion or some other growth or formation to be subjected to thermal ablation. The ultimate goal of the thermal ablation procedure will typically be complete cellular coagulation necrosis of the targeted sub-volume within the VOI. The baseline digital image may generally be a digital rendered three-dimensional image comprised of detected and computed signal data corresponding to an array of spatial locations substantially throughout the VOI.

Prior to capturing the baseline digital image, a preliminary thermal ablation plan may be accessed. The preliminary thermal ablation plan may be accessed from a memory storage module. This plan may include pre-therapy images of the targeted area, along with a preliminary plan of thermal ablation applicator placement, power levels, and times. The baseline digital image may be compared to the pre-therapy images. This comparison may be used to verify tumor and surrounding tissue positions. The image may also be used to verify tumor size and shape. If changes have occurred that surpass a predetermined threshold, the preliminary thermal ablation plan may be updated to take into account the measured differences. For example the tumor may have grown larger or smaller since the therapy planning images were acquired.

The preliminary thermal ablation plan may be accessed from a memory module. The memory module may be present in a system controller, having been stored their prior to the start of the thermal ablation procedure. Alternatively, the thermal ablation plan may be stored remotely from the equipment used during the thermal ablation procedure and retrieved when needed during the thermal ablation procedure. The information contained within the thermal ablation plan may at least be partially stored in a standardized form such as a DICOM data set.

The baseline digital image may be registered to the pre-therapy images so that the planned positions of the applicators to be used in the thermal ablation procedure may be determined relative to the baseline digital image. As described above, registration may be accomplished through the use of the fiducials internal or external to the patient. The fiducials may be locatable by the x-ray imaging system and serve as landmarks within the images to assist software in the alignment of the baseline digital image to the pre-therapy images.

Also as described above, the registration may also be accomplished without the use of artificial fiducials through software.

The capturing of the baseline digital image may comprise illuminating the VOI with a plurality of x-rays and detecting a plurality of portions of the x-rays that have passed through the VOI. A rendered three-dimensional view of the VOI may then be generated using CT methods known to those skilled in the art based on the detected x-rays. As noted above, the x-ray beams used to illuminate the VOI may be a narrow beam, a fan beam, or a cone beam. The x-ray system may be an X-ray C-arm system that can produce cone beam CT images while providing greater access for a physician to interface with the VOI.

Furthermore, the quality and accuracy of the baseline digital image may be enhanced by combining CT generated images with images generated by other imaging modalities. These other imaging modalities may be, for example, ultrasound (including ARFI and or elastography capabilities), Positron Emission Tomography (PET), Single Photon Emission Computed Tomography (SPECT), Magnetic Resonance Imaging (MRI), other molecular imaging methods, or any other modality of generating rendered three-dimensional views of a VOI in a patient known to those skilled in the art. Additionally, these imaging modalities may or may not use contrast agents to enhance the generated images. Furthermore, these additional imaging modalities may employ visualization software to aid in the comprehension of the VOI. Software for enhancing the images and/or information generated by these other imaging modalities may also be used.

The step of capturing 400 a baseline data image set of a VOI may include spatially filtering the baseline data image set. As part of the capturing 400 step, structures within the VOI may be identified. This identification may be automatic or may be performed by an operator or technician as part of the capturing 400 step. For example, if the targeted area of the thermal ablation procedure was a cancerous tumor located within the liver, the VOI may include the liver and some surrounding structures and tissue. Image segmentation software may automatically identify the liver and surrounding structures such as the vena cava. Alternatively, or in combination, structures may be identified by a physician. This identification may take the form of using a software program to select a structure or volume within the captured image and appropriately demarcating or labeling the structure. Physician identified inputs may also be used to guide or constrain image segmentation software which may segment the various tissue structures.

The captured image may be calibrated to determine the relationship between measured HUs and temperature as previously described. By correlating these factors, HU changes measured by subsequent image capturing steps may be correlated to temperature changes. Generally, the capturing 400 of the baseline digital image will take place at the beginning of a thermal ablation procedure. Although an image of the VOI may have been captured earlier and used to develop a thermal ablation plan, a new, current image, may still be captured at the beginning of the thermal ablation procedure. Since the planning image may have been captured on a different scanner or by the currently used scanner at a different time, the new baseline digital image may be used to develop a current temperature correlation between measured HUs and temperature.

The captured baseline digital image may be displayed in a variety of ways. For example, the baseline digital image may be displayed as discussed above in relation to the image display depicted in FIG. 8. The image display may be in the form of a two-dimensional slice wherein a physician selects the orientation and position of the sliced to be displayed. The display may also incorporate elements of the thermal ablation plan. For example, the physician may select to overlay the temperature changes calculated to occur according to the thermal ablation plan throughout the plan procedure. This may take a form similar to the series of images shown in FIGS. 6A through 6E, where each image may depict the planned temperature profile for a separate point in time during the planned thermal ablation procedure. Other methods of presenting rendered three-dimensional views known to those skilled in the art may be used including the use of special glasses to project different images to each of the observer's eyes.

The next step as shown in FIG. 4 may be to perform 401 thermal ablation on at least at first sub-volume of the VOI according to a thermal ablation plan. As noted above, this may be performed with a single thermal ablation applicator or a plurality of thermal ablation applicators wherein the plurality of thermal ablation applicators may operate simultaneously using different modes of thermal ablation delivery. These modes may be interstitial or extracorporeal. These modes may include, but are not limited to, RFA, laser ablation, microwave, focused ultrasound and cryoablation. Accordingly, "thermal ablation" as used in this description refers to therapy where the thermal changes are introduced into a VOI to produce coagulation necrosis in a targeted volume. The thermal changes may either be positive in the case of devices used to heat the targeted coagulation necrosis volume or negative in the case of devices used to lower the temperature within the targeted coagulation necrosis volume.

The positioning and orientation of the thermal ablation applicators is an important aspect in producing the desired target coagulation necrosis volumes. The initial positioning of the thermal ablation applicators may be determined by the thermal ablation plan. The proper thermal ablation applicator positioning may be achieved in several ways.

Ultrasound imaging may be used to assist the physician in the proper location of the thermal ablation applicators. For example, as shown in FIG. 3 a physician 304 may make a preliminary determination of the area in which the applicator 301 is to be inserted using ultrasound imaging. The physician 304 may then insert the thermal ablation applicator 301 and verify the proper position of the thermal ablation applicator 301 by looking at an ultrasound image 306 of the VOI 307 with the applicator 301 inserted. The applicator 301 may be displayed 308 in the ultrasound image 306 relative to the VOI 307. Once the physician 304 is satisfied that the applicator 301 is in the proper location according to the plan, the thermal ablation may be delivered to the VOI 307. The ultrasound image 306 may be overlaid over the baseline digital image. As discussed above, the baseline digital image may be registered to the pre-therapy images and the planned applicator positions may be then transferred to the baseline digital image. Therefore, the baseline digital image may contain the planned applicator positions. Accordingly, when the ultrasound image 306 is overlaid over the baseline digital image, the planned applicator positions may be visible to assist the physician 304 in inserting the applicator 301 in a proper position.

The thermal ablation applicator may be interconnected to a stereotactic, optical tracking, or magnetic tracking positioning system. In such a system, sensors located in proximity to the surgical area are operable to detect the position and orientation of the stereotactic applicator relative to coordinate system in the surgical area. The patient, or at least the VOI in the patient, must also be registered to the coordinate system in the surgical area. In this manner, the orientation and position of the applicator relative to the VOI may be known. The position of the applicator may then be displayed relative to the VOI and may aid the physician in proper applicator placement. Such systems are known to those skilled in the art, and one such system is marketed by General Electric under the name InstaTrak.

Fiducials may be used to assist in registering the VOI of the patient to the coordinate system in the surgical area. These fiducials may be placed on the skin of the patient or internal to the patient and serve as markers visible to imaging systems such as CT scanners and ultrasound imagers and to aid in registering the VOI to the same coordinate system as the applicators. In addition, natural anatomic markers, such as ribs, spine, borders of organs, etc., may be used as internal fiducials for image registration software methods. Accordingly, applicator positioning may be overlaid onto images of the VOI to help guide the physician in inserting the applicator into a proper position according to the plan.

The thermal ablation applicator may be interconnected to a stereotactic applicator positioning system and be mounted on an automated applicator handling system. In this embodiment, once a patient is registered to the same coordinate system as the automated applicator handling system, a robotic arm may be used to position the thermal ablation applicator into the planned position. Although the above discussion was described in terms of a single thermal ablation applicator, systems and methods described may also be used to control and/or locate multiple thermal ablation applicators.

Once the applicator or applicators are in an acceptable position, they may be activated to deliver thermal ablation. The following passages will generally described the thermal ablation as being the introduction of energy into the VOI to produce an increase in temperature in a specific sub-region of the VOI to produce cell coagulation necrosis. However it should be appreciated that cryoprobes may also be utilized in which case the thermal ablation may be performed by removing heat from the VOI to decrease the temperature in a specific sub-region of the VOI to produce cell coagulation necrosis.

Figure 7A:
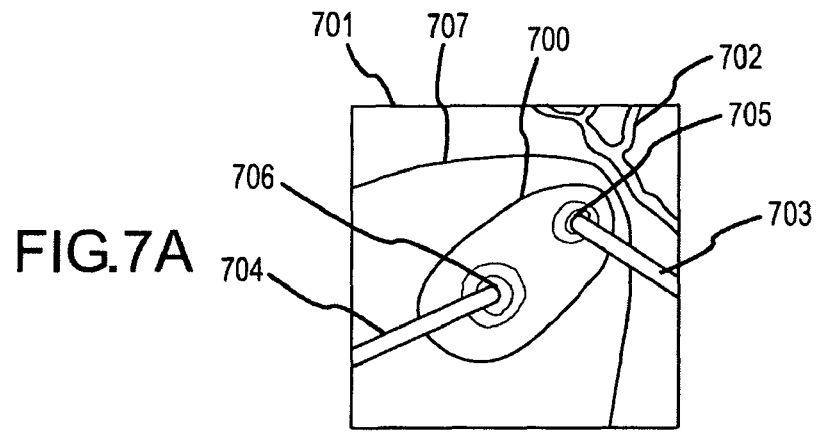
FIGS. 7A through 7C are illustrations of images generated by an embodiment of the present invention depicting isothermal regions within the VOI wherein multiple thermal ablation applicators are being used.
Figure 7B:
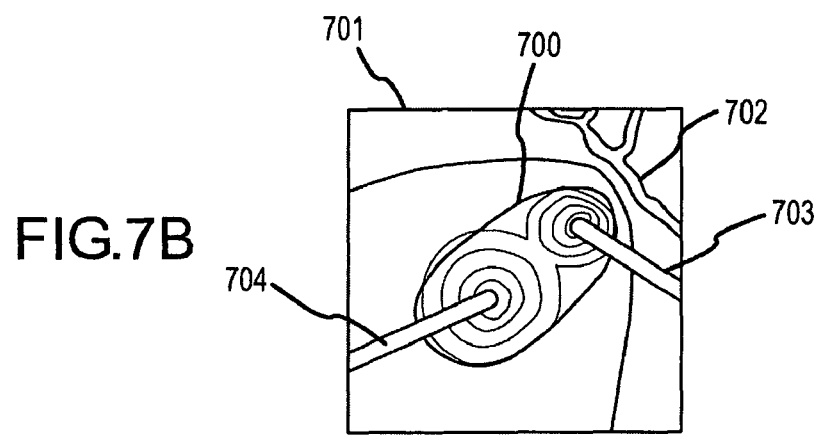
Figure 7C:
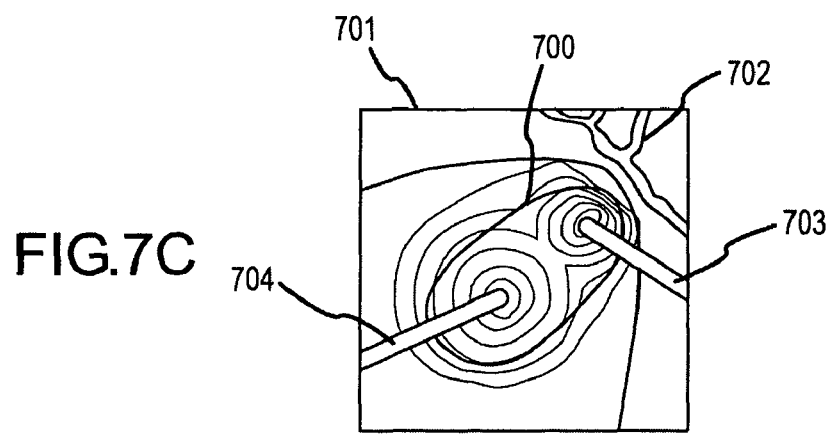

As discussed above, the different modes of thermal ablation delivery may produce different heating effects. For example, focused ultrasound will produce a point source of heat with heat emanating in all directions from that point source, wherein other types of heating, such as bipolar RFA, may be configured to only direct energy primarily to a particular, physician selectable volume. The different properties of different types of heating may be combined to produce coagulation necrosis volumes within tissue shaped to match the targeted areas. Such a situation is illustrated in FIGS. 7A through 7C. FIG. 7A depicts a target coagulation necrosis volume 700 within a VOI 701. The target coagulation necrosis volume 700 may be a cancerous tumor or other lesion where it is desired that the cells of the target coagulation necrosis volume 700 be subjected to elevated temperature to produce coagulation necrosis throughout the target coagulation necrosis volume 700 which may include a thermal surgical margin. However, critical structures that may be damaged by elevated temperatures may be in proximity to the target coagulation necrosis volume 700. In such cases, the application of thermal ablation must be carefully monitored to not damage the critical structure. It should be appreciated that the critical structure may be any structure, such as organs, veins, arteries nerves, bowel, ureter, spinal canal, aorta or vena cava wherein the application of heat to that structure may cause unwanted or serious complications. Therefore, a goal of a thermal ablation plan developed for such a situation may be to produce coagulation necrosis in the target coagulation necrosis volume 700 without producing significantly elevated temperatures in the critical structure.

Also, structures which may act as heat sinks or sources may be within the VOI. In FIGS. 7A through 7C, one such structure is represented by a major vein 702. In such situations it may be beneficial to use different types of heating modes and different types of thermal ablation applicators to achieve the targeted coagulation necrosis. In FIG. 7A, thermal ablation applicators 703 and 704 are applicators operable to uniformly deliver energy in all directions relative to the applicator tips 705 and 706. However, the vein 702 may act as a heat sink as flowing blood carries away the heat energy produced by the thermal ablation applicator 703. Therefore the thermal ablation applicator 703 must be positioned as to take into account the target coagulation necrosis volume 700 and the heat sink characteristics of the vein 702. As can be seen from FIGS. 7A through 7C, this positioning of applicators may be operable to produce sculpted elevated temperatures within the target coagulation necrosis volume 700 despite the heat sink effect of the vein 702. The circular bands emanating from the applicator tips 705, 706 represent isothermal bands depicting regions of elevated temperatures. As discussed above, the isothermal regions may be color-coded to represent specific temperature ranges thereby communicating with the physician the progress of the thermal ablation. The relative closeness of the isothermal bands in the region between the applicator tip 705 and the vein 702 represent a greater temperature gradient in that direction due to the flowing blood in the vein 702 carrying away heat.

FIG. 7 illustrates the use of two monopolar thermal ablation applicators to deliver the thermal ablation to the VOI. The applicators may also be bipolar where energy is delivered to a region between the nodes of the thermal ablation applicator. For example, an RF electrode may be bipolar where two sets of multiple tines each form a node and the heat inducing RF energy is directed between the nodes, preferentially heating the region between the nodes.

As the thermal ablation is being performed, certain events may trigger the system to capture an x-ray or x-ray CT image of the VOI. The trigger may be the passage of a predetermined amount of time as per the thermal ablation plan. For example, the plan may include capturing an x-ray CT image after performing thermal ablation for one minute. In another embodiment, the capturing of a subsequent x-ray CT image may be triggered by the amount of energy deposited into the VOI through the thermal ablation applicators. In another embodiment, the capturing of a subsequent x-ray CT image may be triggered by a request from a physician performing the thermal ablation procedure. Alternatively, additional and complementary imaging modalities may be incorporated to determine when an x-ray CT image of the VOI should be generated. For example, ultrasound may be used to detect changes to tissue within the VOI that may indicate changes in temperature. Changes detectable by ultrasound may include changes such as charring, coagulation, or percolation in the targeted area. Once such changes are detected by ultrasound, the ultrasound controller 309 may send a signal to the system controller 104 which may subsequently request or direct the x-ray imaging system to produce an x-ray CT image of the VOI.

Ultrasound systems with ARFI or elastography capabilities may be used to trigger the capture of additional x-ray CT images. Such systems may be operable to detect mechanical changes (e.g., elastic tissue properties) associated with the elevation in temperature caused by thermal ablation. These detected changes may then be fed into the system controller 104 and once they surpass a predetermined threshold, the system controller 104 may direct the x-ray imaging system 102 to capture an x-ray CT image of the VOI. ARFI and other ultrasound methods including elastography (strain imaging) methods use nominally diagnostic ultrasound power range sound waves to produce images. While there are concerns and regulatory limits concerning tissue heating from ultrasonic power deposition in tissues, when used to monitor the effects of ablative heat sources there is little added concern about long-term effects of exposure to these procedures. However, these imaging modalities may only serve to indicate gross tissue property changes when compared to the relatively fine temperature changes that may be able to be detected by the x-ray CT scanner. Therefore, the ARFI, elastography and other ultrasound imaging modalities may be used throughout the thermal ablation procedure to monitor for temperature related changes reducing the amount of x-ray images needed during the thermal ablation procedure.

The next step of the method illustrated in FIG. 4 may be to capture 402 a first temperature differential image of the VOI. As described immediately above, the capture 402 may be triggered in a variety of ways. Although the ultrasound imaging systems (including ARFI and elastography capable systems) discussed above may be operable to detect changes which are indicative of temperature changes, the term "temperature differential image" used herein refers to x-ray or x-ray CT images which, when compared to other x-ray or x-ray CT images, may be operable to determine relatively small temperature variations throughout the VOI. The first temperature differential digital image (and subsequent temperature differential digital images if required) may be an image substantially corresponding to the same spatial volume as the baseline digital image. The first temperature differential digital image may be captured with the same equipment in substantially the same configuration as was used to capture the baseline digital image. The image may be generated using substantially the same techniques as those used to generate the baseline digital image. Also similar to the baseline digital image, additional imaging modalities may be used to enhance the first temperature differential digital image, and the first temperature differential digital image may be filtered. Finally, the first temperature differential digital image may be displayed separately from, but in a similar fashion to, the baseline digital image.

The delivery of thermal ablation may be suspended during the capturing 402 of the first temperature differential digital image. Alternatively, the thermal ablation applicators may remain active during the process of capturing the first temperature differential digital image. As discussed above, the configuration of the CT scanner, such as the C-arm configuration, may allow the applicators to remain in place during the imaging process and therefore there may be no need to move the patient for imaging or thermal ablation delivery. Therefore the patient may remain stationary throughout the entire thermal ablation procedure. This is advantageous in that no re-registration may be required during the thermal ablation procedure.

The next step of the method illustrated in FIG. 4 may be to register 403 the first temperature differential digital image to the baseline digital image. As described above, registration may be accomplished through the use of fiducials internal or external to the patient or through software. The computational requirements of the registration process may be greatly simplified if the patient has remained stationary since the capture of the baseline digital image. The reduced computational requirements may result in a faster registration process. If the patient has moved since the capture of the baseline digital image, the registration of the first temperature differential digital image to the baseline digital image may be performed in a similar fashion to the registration of the baseline digital image to the pre-therapy images. That is, the registration may be performed using hardware such as fiducials or without fiducials using software which functions by aligning elements of the two images.

The next step of the method illustrated in FIG. 4 may be to infer 404 temperature changes at substantially each spatial location within the VOI. This inference may be made based on the baseline digital image and the first temperature differential digital image. At each measured spatial location within the VOI, radiodensity or HU data for the first temperature differential digital image may be subtracted from data from the baseline digital image. The resulting difference for each spatial location may be a result of radiodensity changes due to temperature changes. Since, as previously described, the HU data may be calibrated, the resulting calculated differences for each spatial location may be converted into a temperature differential for each spatial location.

The temperature differentials inferred for each spatial location may be aggregated and displayed to communicate temperature changes throughout the VOI in an inferred temperature changes image. As discussed earlier with respect to the apparatus disclosed herein, the display may be in the form of a two-dimensional slice through the VOI or a representation of the VOI in three dimensions may be provided. The location of the two-dimensional slice or three-dimensional region may be selected by the physician or generated by the system. For example, FIG. 6A may illustrate a baseline digital image showing a thermal ablation applicator 604 inserted into an internal structure 605 prior to any application of thermal ablation. The internal structure 605 may be an organ such as a liver. Alternatively, the structure may be a breast, prostate, lung, kidney, or any other organ or region where a tumor or other thermal ablation target may be located. Subsequently, a first temperature differential digital image may be captured and subtracted from the baseline digital image to produce a data set representative of changes in temperature throughout the VOI. This data set may then be superimposed over the baseline digital image to produce an inferred temperature changes image as shown in FIG. 6B where the demarcated region 602 represents a region of elevated temperature over the temperature prior to the application of any thermal ablation. The demarcated region 602 may be indicated by an isothermal line representing an isothermal surface within the VOI 601. Alternatively, the demarcated region 602 may be indicated by a shaded isothermal region. The isothermal lines or regions may be color-coded and a legend may be provided to communicate to a physician temperature changes induced throughout the VOI 601. The legend and isothermal line or region may be in terms of temperature differentials or absolute temperatures. For example, the demarcated region 602 may represent an area that is generally 8° C. warmer relative to the surrounding area of the internal structure 605 or the demarcated region 602 may represent an area that is generally at about 45° C. whereas the rest of the internal structure 605 may be indicated to be at 37° C. Generally, the apparatus described herein may be capable of discerning and displaying changes in temperature in the VOI in 15° C. or smaller increments. In many circumstances, displaying temperature changes or differences in 15° C. increments provides sufficient information to determine if the coagulation necrosis goals have been met. As discussed above, resolution and scanning time are interrelated. Therefore, 15° C. increments may be used to keep scan times and x-ray exposures to a minimum. However, through signal-to-noise ratio reduction techniques such as extending the scan times of the x-ray CT scanner or averaging multiple x-ray CT scans and filtering the image data sets, the apparatus described herein may be capable of discerning and displaying changes in temperature in the VOI in 1° C. increments.

The inferred temperature changes image may also represent temperature changes in three dimensions. This may be displayed in a manner similar to that described above with reference to FIG. 8.

A predicted coagulation necrosis volume may be calculated based on the inferred temperature changes. This prediction, which is an estimate as to the extent of tissue destruction, may be based on the time vs. temperature profile experienced by a particular area within the VOI. The coagulation necrosis volume prediction may also be accompanied by information as to the rate of change of the predicted coagulation necrosis volume. The calculations may be performed on a computer and may use methods such as finite element analysis or other computational methods to generate the prediction. Brief exposure to massive temperature changes (for example 50° C. above normal body temperature for one minute) as well as prolonged exposure to milder temperature changes (for example 10° C. above normal body temperature for one hour) may eventually produce cell coagulation necrosis. In the case of massive temperature changes, the cell coagulation necrosis may be detectable immediately as charred or otherwise physically damaged volumes. In the case of prolonged exposure at milder temperature changes, the cell coagulation necrosis may occur over time after the thermal ablation procedure is completed and may not be immediately detectable. In either case, the present method may include the step of predicting the eventual volume of necrotic cells caused by the thermal ablation procedure. This prediction may be dynamic in that it may be continually updated during a thermal ablation procedure to reflect the effects of additional thermal ablation being applied during the procedure. The predicted coagulation necrosis volume made be displayed as an overlay similar to the displays previously discussed. The predicted coagulation necrosis volume may also be displayed relative to the target coagulation necrosis volume.

The next step of the method illustrated in FIG. 4 may be to compare 405 the inferred temperature changes to the expected temperature changes from a thermal ablation plan. This comparison may compare the changes inferred at substantially each spatial location within the VOI to the expected temperature changes at each spatial location within the VOI. If this comparison reveals a difference between the inferred temperature changes and expected temperature changes that is not greater than a predetermined level, the next step may be to continue the thermal ablation procedure according to the thermal ablation plan. However, if this comparison reveals a difference between the inferred temperature changes and expected temperature changes that is greater than a predetermined level, the thermal ablation plan may be adjusted or modified to create a second thermal ablation plan. The second thermal ablation plan may be designed to compensate or correct for the deviations between the inferred temperature changes and the expected temperature changes to achieve the coagulation necrosis goals. The comparison may be performed by at least one computer. The adjustments to the thermal ablation plan may be determined by computer algorithms.

The second thermal ablation plan may be stored in a memory module. The memory module may be present in the system controller. The second thermal ablation plan may also be stored remotely from the equipment used during the thermal ablation procedure. The information contained within the second thermal ablation plan may at least be partially stored in a standardized form such as a DICOM data set.

The adjusting of the thermal ablation plan may include adjusting the power output of the thermal ablation applicators, the orientation or direction of the output of the thermal ablation applicators, and the target point of the thermal ablation applicators. Some thermal ablation applicators may be operable to change the focal point for the delivery of the thermal ablation without changing the physical location of the device. For example, in the case of laser ablation fibers, methods of directing the laser light through intra-catheter collimation or catheter rotation may alter the tissue field to which the ablative energy is directed. Similarly, the power and control directed to an ultrasound applicator may change the area that may receive energy from the applicator.

The position of the applicator may also be adjusted or repositioned. These adjustments may be performed by the physician, wherein the physician adjusts the characteristics of the output of some or all of the thermal ablation applicators or repositions some or all of the thermal ablation applicators. Alternatively, these parameters may be adjusted automatically by the system controller. In the case of device repositioning, this may be adjusted automatically by the system controller in embodiments that include robotic manipulation of the thermal ablation applicators. The system controller may also determine that to best achieve the coagulation necrosis goals a different quantity of thermal ablation applicators or a different type of thermal ablation applicators may be required. All of the above-mentioned adjustments may then be incorporated into an updated second thermal ablation plan.

These adjustments may be performed in a closed-loop feedback control system. The closed-loop may be comprised of the system controller that may be operable to adjust parameters of the thermal ablation procedure, the x-ray or x-ray CT scanner that may then detect changes as a result of the adjustment of parameters and subsequently feed the changes back to the system controller which may make further parameter adjustments. In this sense, the system controller, x-ray or x-ray CT scanner, and the thermal ablation applicators form a closed-loop control system. In this regard, the system may have the ability to control the extent of the ablative zone dynamically through computer control. The physician may then be able to monitor the status of the ablative zone as well as the overall condition of the patient. Data regarding the estimated time to completion of the thermal ablation procedure may also be generated and displayed.

While monitoring the status of the ablative zone and the overall condition of the patient, the physician may make the determination to alter various parameters of the thermal ablation procedure. Under these circumstances, the system controller may recalculate a predicted coagulation necrosis volume based on the new parameters initiated by the physician. This new predicted coagulation necrosis volume may then be displayed for the physician to inform the physician of potential effects of the altered parameters.

The next step of the method illustrated in FIG. 4 may be to continue 406 the thermal ablation according to the updated second thermal ablation plan. The second thermal ablation plan may target a different sub-volume of the VOI than was targeted by the original thermal ablation plan. As shown in FIG. 4, the next step may be to return to step 402 and capture an additional temperature differential digital image. The capturing of the additional temperature differential digital image may be triggered in the same manner as the first temperature differential digital image (e.g. passage of time, etc.). This may be followed by repeating step 403 and registering the additional temperature differential digital image to the baseline digital image and then inferring 404 temperature changes across the VOI. If at this point, the calculated predicted coagulation necrosis volume meets the coagulation necrosis goals, the thermal ablation procedure may be halted. Otherwise, the next step may be to compare 405 the newly determined inferred temperature changes to the expected temperature changes and adjust the thermal ablation plan accordingly and continue the thermal ablation procedure. This loop of capture 402, register 403, infer 404, compare 405, and continue 406 may continue until the predicted coagulation necrosis volume meets the coagulation necrosis goals.

Figure 6F:
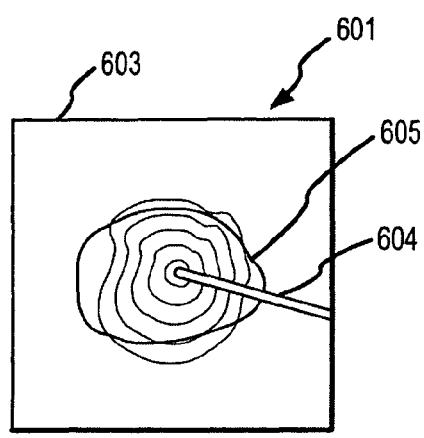

During the procedure, the physician may select to have the inferred temperature changes images all displayed relative to the baseline digital image. In other words, each subsequently generated inferred temperature changes image may display temperature changes relative to the temperature of the VOI measured at the time of the capturing of the original baseline digital image. Such a series of images is illustrated in FIGS. 6A through 6F. FIG. 6B illustrates a first inferred temperature changes image wherein the demarcated region 602 is indicative of a small temperature change occurring in the early stages of a thermal ablation procedure. The inferred temperature changes images have been overlaid over the baseline digital image in FIGS. 6B through 6F. The demarcated region 602 may, for example, indicate a region that is at least 8° C. above the surrounding area. As the thermal ablation applicator 604 continues to introduce energy into the VOI 601, the volume within the VOI 601 experiencing elevated temperatures will increase in size. This is illustrated by the subsequent inferred temperature changes images shown in FIGS. 6C through 6E. In these figures, each demarcated region may denote a particular range of temperatures. For example, in FIG. 6E, the non-demarcated region (the region outside of line 606) may represent areas within the VOI 601 that have not experienced more than a 8° C. rise in temperature. The area between line 606 and line 607 may represent an area within the VOI 601 that has experienced a rise in temperature between 8° C. and 16° C. Similarly, the area between line 607 and line 608 may represent an area within the VOI 601 that has experienced a rise in temperature between 16° C. and 24° C. In this manner the lines provide a temperature or thermal map of the VOI where the individual regions represent 8° C. temperature differences. As noted above, isothermal regions may be used to communicate temperatures throughout the VOI 601 in which case of the area between lines 606 and 607 may be shaded in a particular color that corresponds with a rise in temperature between 8° C. and 16° C. Similarly, the area between line 607 and line 608 may be shaded in another color to represent an area within the VOI 601 that has experienced a rise in temperature between 16° C. and 24° C. FIG. 6F may represent an inferred temperature changes image generated subsequent to the repositioning of the thermal ablation applicator 604, which as discussed above, may be required to achieve the coagulation necrosis goals.

Alternatively, the physician may select to have the inferred temperature changes images displayed relative to any previously captured temperature differential image. For example, the physician may elect to have an image displayed that only reflects the temperature differences between the latest image generated by the x-ray or x-ray CT scanner and the previous image generated by the x-ray or x-ray CT scanner. In this regard, the inferred temperature changes image may reflect temperature changes that have occurred between the latest two temperature differential digital image capture times. This may be useful to the physician to highlight aspects of how temperature changes are progressing during the thermal ablation procedure.

After the thermal ablation portion of the thermal ablation procedure has been completed, additional temperature differential images may be captured to record temperatures within the VOI as they return to normal or stable body temperature. The thermal ablation procedure may include the step of generating a report or record of the procedure. The report may be archived along with images and may at least partially follow the Digital Imaging and Communications in Medicine Structured Reports (DICOM SR) model.

FIG. 9 is a flowchart of an additional method of performing thermal ablation within a VOI in a patient. The first step of the method is to position 900 a patient within a field of view of an imaging device. Once the patient is positioned the patient may remain stationary throughout the entire thermal ablation procedure of the present method. The image capture device used may be an x-ray Cone Beam Computed Tomography (CBCT) C-arm scanner with a two-dimensional flat-panel sensor array to detect the x-rays.

The next step as shown in FIG. 9 may be to capture 901 a baseline digital image of a VOI in a patient with an x-ray system. This step may be similar to the capturing step 400 described in relation to the method illustrated in FIG. 4. Similar to the capturing step 400, the capturing step 901 may include augmenting or enhancing the images generated by the x-ray C-arm CBCT scanner with other imaging techniques such as ultrasound, ARFI, PET, SPECT, NI, and/or other imaging methods. These other techniques may incorporate contrast agents to improve image quality. The image generated by the x-ray C-arm CBCT scanner may also be calibrated using methods similar to those previously described.

The next step as shown in FIG. 9 may be to perform 902 thermal ablation on at least at first sub-volume of the VOI according to a thermal ablation plan. This step may be similar to the performing step 401 described in relation to the method illustrated in FIG. 4. This step is followed by capturing 903 a first temperature differential digital image. The step may be followed by adjusting 904 a thermal ablation plan based at least in part on the differences between the baseline digital image and the first temperature differential digital image. The adjusting 904 of the thermal ablation plan may create an adjusted thermal ablation plan. The adjusted thermal ablation plan may be stored in a memory module. The memory module may be present in the system controller and/or remote from the equipment used during the thermal ablation procedure. The information contained within the adjusted thermal ablation plan may at least be partially stored in a standardized form such as a DICOM data set.

The thermal ablation may then be continued 905. Additional cycles of capturing 903 temperature differential digital images, adjusting 904 the thermal ablation plan, and continuing 905 the thermal ablation procedure may be repeated until predicted coagulation necrosis volumes meet coagulation necrosis targets.

FIG. 10 is a flowchart of a method of inferring thermal changes within a VOI in a patient occurring during a thermal ablation procedure. The first step of the method is to capture 1000 a baseline digital image of a VOI in a patient wherein the baseline digital image contains data corresponding with a baseline array of spatial locations substantially throughout the VOI. Each spatial location may be a voxel representing a volume of at most 1 cm$^3$. The capturing 1000 of the baseline digital image may be performed at least in part by an x-ray or x-ray CT scanner. The x-ray or x-ray CT scanner may use a cone shaped x-ray beam and a two-dimensional x-ray detection array to generate the baseline digital image.

The next step of the method is to perform 1001 thermal ablation on at least a first sub-volume of the VOI. The thermal ablation may take the form of elevating or lowering temperatures within the sub-volume of the VOI in order to induce cellular coagulation necrosis in the sub-volume.

The next step of the method is to capture 1002 a first temperature differential digital image of the VOI. Similar to the baseline digital image, the first temperature differential digital image contains data corresponding with a first temperature differential digital image array of spatial locations substantially throughout the VOI. The following step is to register 1003 the first temperature differential digital image to the baseline digital image. The image registration may be performed as the image registration described previously with respect to the method illustrated in FIG. 4.

The next step is to calculate 1004 the image signal data changes between the first temperature differential digital image and the baseline digital image for substantially each spatial location within the first temperature differential digital image array. This step may take the form of comparing the measured value at each spatial location or voxel of the first temperature differential digital image array with the measured value at each corresponding spatial location or voxel of the baseline digital image. The comparison may take the form of subtracting HU measurements for each spatial location of the first temperature differential digital image from HU measurements for each spatial location of the baseline digital image. The result of this comparison may be a spatial array representing changes in HU measurements for each spatial location of the first temperature differential digital image array.

The final step of the method is to infer 1005, based at least in part on the calculated image signal data changes, temperature changes at substantially each spatial location within the first temperature differential array from the results of the calculating step 1004. The inferred temperature changes may be displayed in a manner to communicate to a physician the inferred temperature changes across the VOI.

The patient may be stationary during the entire method illustrated in FIG. 10. The patient may be positioned prior to the capturing of the baseline digital image and that position may be maintained throughout the entire thermal ablation procedure.

FIG. 11 is a flowchart of a method of predicting a coagulation necrosis volume caused by a thermal ablation procedure. The first step of the method is to capture 1100 a baseline digital image of a VOI in a patient wherein the baseline digital image contains data corresponding with a baseline array of spatial locations substantially throughout the VOI. The capturing 1100 of the baseline digital image may be performed at least in part by an x-ray or x-ray CT scanner. The x-ray or x-ray CT scanner may use a cone shaped x-ray beam and a two-dimensional x-ray detection array to generate the baseline digital image.

The next step of the method is to perform 1101 thermal ablation on at least the first sub-volume of the VOI according to at least a portion of a thermal ablation plan. The next step of the method is to capture 1102 a first temperature differential digital image of the VOI followed by registering 1103 the first temperature differential digital image to the baseline digital image.

The next step is to calculate 1104 the image signal data changes between the first temperature differential digital image and the baseline digital image for substantially each spatial location within the first temperature differential digital image array and then infer 1105, based at least in part on the calculated image signal data changes, temperature changes at substantially each spatial location within the first temperature differential array from the results of the calculating step 1104.

The next step is to predict 1106 a coagulation necrosis volume caused by the thermal ablation performed during the thermal ablation procedure. The predicted coagulation necrosis volume may be calculated real-time or it may be calculated for a user selected point during the thermal ablation procedure. For example, a physician may choose to calculate and display a real-time predicted necrosis volume during the thermal ablation procedure. The physician may also choose to display the predicted coagulation necrosis volume at various points earlier in the thermal ablation procedure, perhaps to review and better understand the development and behavior of the predicted coagulation necrosis volume throughout the thermal ablation procedure.

The prediction of coagulation necrosis based on time-temperature integration may take into account factors such as the time-temperature profile seen by cells during the thermal ablation procedure (including the cooling period after thermal ablation as the cells return to normal body temperature) and the types of cells. For example, it is known to those skilled in the art that cell death may be caused by relatively short periods of exposure to temperatures above 50° C. However, cellular death may also be caused by longer exposure to temperatures above normal body temperature but below 50° C. The death may occur over time after the cells have returned to normal body temperature. Basing predicted necrosis volume on time-temperature integration takes these factors into account to predict the ultimate coagulation necrosis volume caused by the thermal ablation procedure.

The next step, not illustrated in FIG. 11, may be to display an at least two-dimensional image of at least a portion of the VOI wherein the display includes at least one of the following features: a planned coagulation necrosis volume; colored isothermal regions representing temperature within at least portion of the VOI; colored isothermal regions representing temperature changes relative to temperatures at the commencement of the thermal ablation; colored isothermal regions representing temperature changes relative to the physician selected point in time occurring earlier during the thermal ablation procedure; a predicted coagulation necrosis volume based on time-temperature integration caused by the thermal ablation up to the physician selected point in time; and colored regions representing inferred temperature variances relative to planned temperature distribution from the thermal ablation plan at a physician selected point in time. The display may be a Multi-Planar Reformatted display or a three-dimensional volume rendered display. The display may be in the form of a combination of these techniques or any other display technique known to those skilled in the art.

Figure 5A:
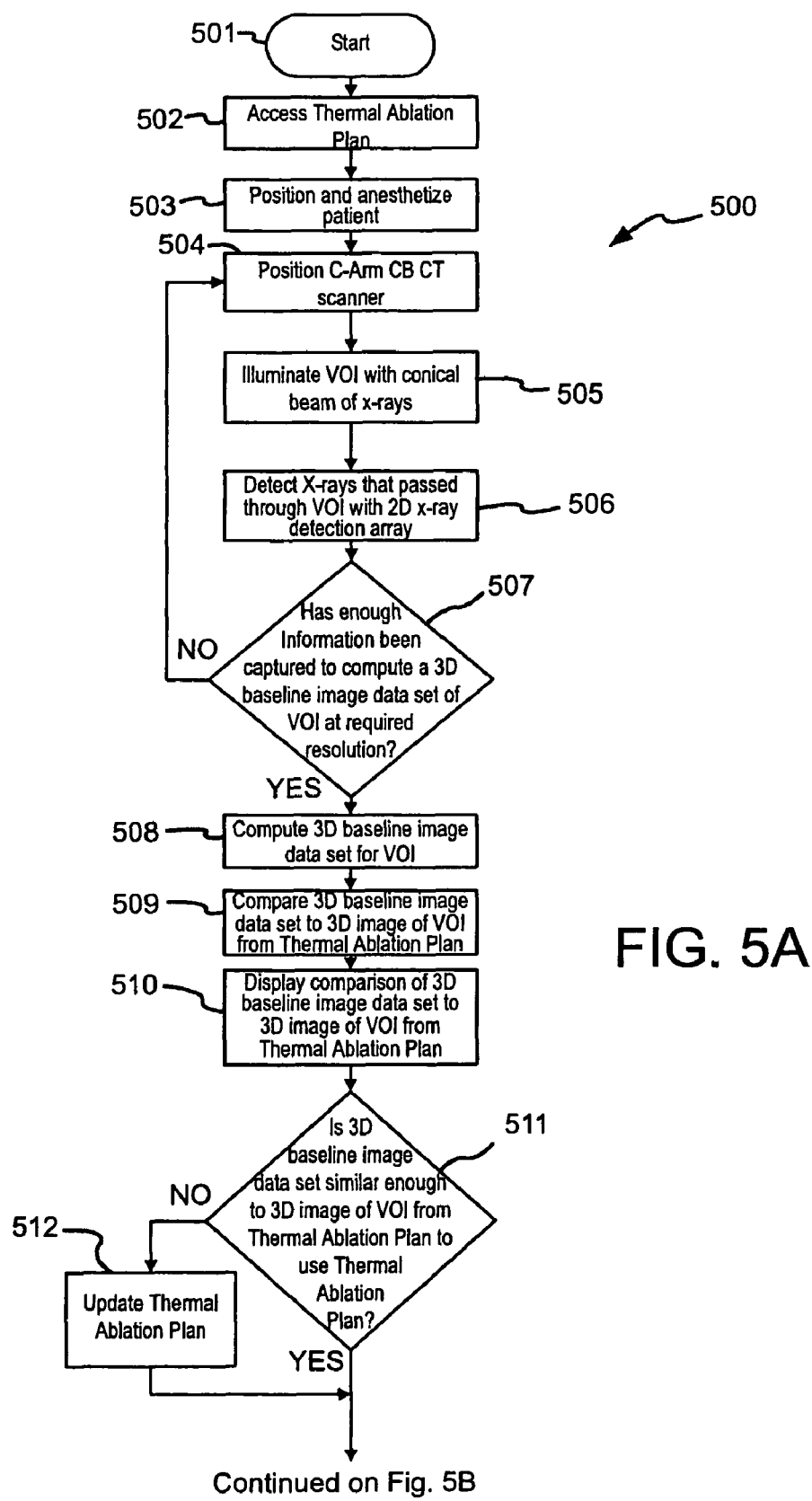
FIGS. 5A and 5B illustrate a flowchart for a method of performing thermal ablation within a Volume Of Interest (VOI) in a patient in accordance with an embodiment of the present invention.
Figure 5B:
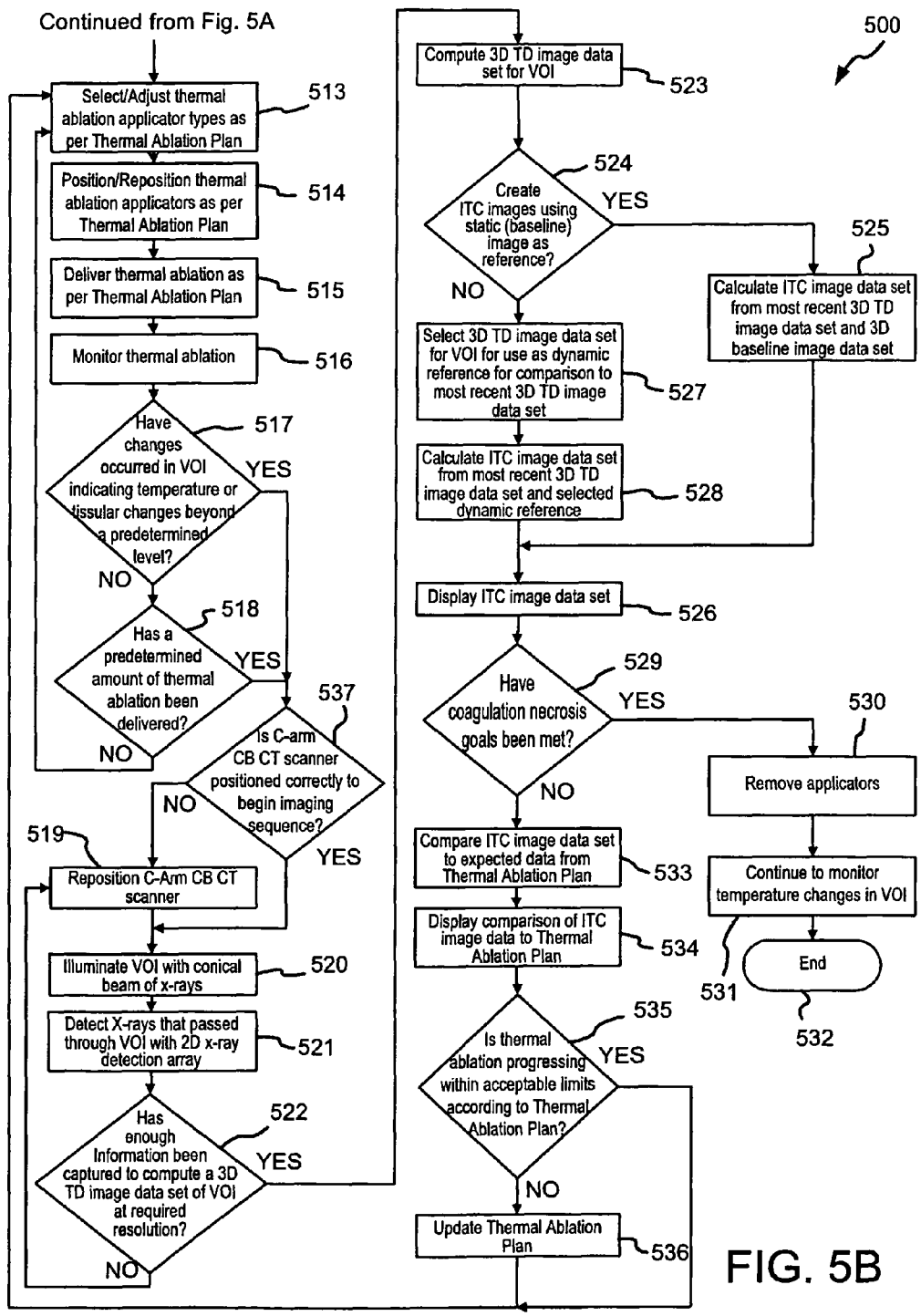

FIGS. 5A and 5B contain a flowchart of a method 500 of performing an entire thermal ablation procedure. The previously discussed flowcharts in FIGS. 4 and 9-11 illustrated the performance of specific portions of a thermal ablation procedure whereas FIGS. 5A and 5B illustrate a thermal ablation procedure from the step of accessing 502 a thermal ablation plan to monitoring 531 temperature changes in a VOI as the VOI returns to normal temperature after the removal of all applicators.

To start 501 a thermal ablation procedure the first step may be to access 502 a thermal ablation plan. The thermal ablation plan may have been previously developed from previously captured images of a tumor (or tumors) and/or other structure (or structures) to be subjected to thermal ablation (hereinafter referred to as the coagulation necrosis target). The previously captured images may also encompass a VOI surrounding the coagulation necrosis target. The VOI may include critical structures, as discussed above, wherein it is desirable that exposure of the critical structures to the thermal ablation be limited. The thermal ablation plan may also include a script of events to occur during the thermal ablation procedure. The script may include details such as applicator type as a function of time, applicator quantity as a function of time, applicator position as a function of time, applicator power levels as a function of time, and expected temperatures throughout the VOI at any given point during the thermal ablation procedure. The thermal ablation plan may have been developed with knowledge of the specific capabilities of embodiments of apparatuses for performing thermal ablation disclosed herein.

The thermal ablation plan may be stored locally in the area where the thermal ablation procedure is to be performed. For example, the thermal ablation plan may have previously been stored on the system controller 104. The thermal ablation plan may also have been stored remotely and may be accessed by the system controller 104 over a network or loaded on to the system controller 104 from a portable data storage device.

After the thermal ablation plan has been accessed 502, the next step may be to position and anesthetize 503 the patient. The thermal ablation plan may have included a specific patient position to provide access to the VOI within the patient for optimal performance of the thermal ablation plan. The patient may be positioned on a table or surface made of materials substantially transparent to x-rays, such as carbon fiber. The table may be movable and its movement may be controlled to position the patient within the field of view of an x-ray scanner. The patient may remain substantially stationary relative to a patient bed throughout the entire thermal ablation procedure. During the thermal ablation procedure, the patient bed may not need to be moved substantially more than a maximum lineal dimension of the VOI. For example, the only patient movement during the thermal ablation procedure may be the movement of the patient bed relative to the x-ray system during imaging. Additionally, the x-ray system may be operable to translate in the direction perpendicular to the vertical plane in which the x-ray source and detector may rotate. In such an embodiment, the patient and patient bed may remain stationary throughout the entire thermal ablation procedure.

Also, the scanner may be operable to image a three-dimensional volume without translating. Such configurations include where the scanner is operable to raster a one-dimensional scan beam across a second dimension, or where the scanner is operable to produce a conical x-ray beam. Such scanners may be operable to produce a three-dimensional image of the VOI with no substantial patient movement, allowing the patient and patient bed to remain stationary throughout the entire thermal ablation procedure.

The x-ray system may be an x-ray CT scanner, an x-ray C-arm scanner, an x-ray Cone Beam Computed Tomography (CBCT) scanner or any combination thereof. For illustrative purposes, the current methodology will be described using an x-ray C-arm CBCT scanner.

Once the patient is positioned and anesthetized 503 to be immobile during the thermal ablation procedure, a baseline three-dimensional image data set of the VOI may be captured prior to the application of any thermal ablation. This step may be needed since a significant amount of time may have passed between the time that the images were captured that formed the basis for the thermal ablation plan and the scheduled thermal ablation procedure. During this time the coagulation necrosis target may have grown, shrunk, or otherwise changed position, shape or size. Structures surrounding the coagulation necrosis target may have also changed.

The first step in capturing the baseline image of the VOI may be to position 504 the C-arm CBCT scanner so that the VOI is within the field of view of the scanner. Since, in a C-arm CBCT scanner, the x-ray source and x-ray detector are connected by a structure that is open or openable, a C-arm CBCT scanner may be moved into and out of an imaging position without moving the patient. Also, the open design of a C-arm CBCT scanner may allow devices, such as sensors or applicators, to remain in place with respect to the patient while the C-arm CBCT scanner captures images of the VOI. Once the C-arm CBCT scanner is in position 504, the next step may be to illuminate 505 the VOI with a conical beam of x-rays. Since the beam is conical, more information may be captured with a single emission and detection cycle than may be captured with a fan shaped beam or narrow beam of x-rays. Next, x-rays that have passed through the VOI may be detected 506 with a two-dimensional x-ray detector array. The next step may be for the C-arm CBCT scanner to determine 507 if enough information has been captured in the performed emission and detection cycles to generate a rendered three-dimensional view of the VOI at at least a predetermined required resolution. If enough information has not been gathered to generate the rendered three-dimensional view of the VOI, the system may return to step 504 and perform another cycle of positioning 504 the C-arm CBCT scanner, illuminating 505 the VOI, and detecting 506 x-rays that have passed through the VOI. The system may then again make the determination 507 if enough information has been captured to generate a rendered three-dimensional view. This cycle may continue until enough information has been gathered to generate a rendered three-dimensional view of the VOI at which point, a three-dimensional baseline image data set for the VOI may be computed 508. At this point, the C-arm may be positioned to allow for maximum access to the VOI, or the C-arm may be withdrawn from the area around the VOI. The three-dimensional baseline image data set may then be displayed using methods known to those skilled in the art. The next step may be to compare 509 the three-dimensional baseline image data set to a three-dimensional image data set of the VOI from the thermal ablation plan. This comparison may compare the coagulation necrosis target of the thermal ablation plan to the coagulation necrosis target of the three-dimensional baseline image data set. Surrounding structures from each data set may also be compared. The thermal ablation plan which contains the three-dimensional image data set of the VOI to be compared to the three-dimensional baseline image data set may be accessed from a memory storage module such as a networked computer or portable memory storage device.

The next step may be to display 510 the comparison of the three-dimensional baseline image data set to the three-dimensional image data set of the VOI from the thermal ablation plan. This may allow the physician to review any changes that may have occurred between the time of the original imaging for the thermal ablation plan and the time of capture of the baseline image data set. Also within this display 510 may be a display of the planned positions of any applicators to be used in the planned thermal ablation procedure along with expected temperature changes throughout the VOI as a function of time during the planned thermal ablation procedure.

The next step may be to determine 511 if the three-dimensional baseline image data set is similar enough to the three-dimensional image data set of the VOI from the thermal ablation plan to use the thermal ablation plan as is. This step may be performed by the system controller and then presented to the physician for approval. In other words, the system controller may make a determination that the plan may or may not be able to be used as is and present this information to the physician at which point the physician may agree with the system controller or override the determination of the system controller. This determination may be made on the basis of a comparison of the size, shape or other parameter of the coagulation necrosis target at the time of the capture of the image of the VOI used by the thermal ablation plan to the coagulation necrosis target at the time of the capture of the three-dimensional baseline image data set. If the physician determines that no changes significant enough to warrant the alteration of the thermal ablation plan have occurred, the thermal ablation procedure may proceed according to the original thermal ablation plan. This determination by the physician may be a result of the physician agreeing with a determination by the system controller that the original thermal ablation plan is adequate or it may be a result of the physician overriding a determination by the system controller that the original thermal ablation plan should be modified prior to proceeding. In another embodiment, the system controller may simply present the information to the physician and the entire comparison and determination of whether or not to proceed with the thermal ablation plan as originally constructed may be made by the physician.

If the determination 511 is made that enough changes have occurred in the VOI to warrant changes to the thermal ablation plan, the next step may be to update 512 the thermal ablation plan. This update may include alteration of any of the plan parameters discussed above, including applicator parameters or patient position. This alteration of the thermal ablation plan may be performed by the system controller 104 (automatically or with the approval of the physician) or by the physician.

After it has been determined 511 that the thermal ablation plan may be used as is or after the thermal ablation plan has been updated 512, the thermal ablation procedure may continue. The first step of the procedure may be to select 513 the thermal ablation applicator types as per the current thermal ablation plan. This selection 513 may include multiple applicator types and/or multiple applicators of those multiple applicator types. The next step may be to position 514 the selected thermal ablation applicators as per the thermal ablation plan. This positioning 514 may be performed in a variety of ways known to those skilled in the art. For example, the applicator positioning may be performed manually using image guided positioning. An image of the desired applicator position (from the thermal ablation plan) may be overlaid or projected onto an image of the VOI. Moreover, an image of the real-time position of the applicator may also be overlaid or projected onto the image of the VOI to help guide, and provide feedback to, the physician to attain the proper applicator position. This real-time image guided positioning may, for example, use CT or ultrasound imaging to register, capture and display real-time applicator position as it is being positioned within the VOI. This image guided positioning may also supply data to the physician regarding actual applicator position relative to planned applicator position. Such data may include, for example, a distance between the planned applicator positioning and the current real-time positioning of the applicator. The positioning may then be verified by the x-ray system or a supplemental imaging method such as ultrasound. The applicators may be equipped with devices or features which may enable a stereotactic positioning system to monitor the real-time position of the applicators with respect to the VOI to help guide the physician to a proper applicator position. Alternatively, some or all of the applicators may be mounted to robotic arms which may then automatically position the applicators within the VOI according to the current thermal ablation plan.

The positioning 514 of the applicators may not be within acceptable tolerances of the planned positions contained in the thermal ablation plan. This may occur for several reasons. For example, there may be internal structures within the patient that prevent applicator placement in accordance with the plan or the physician may simply miss the targeted applicator placement. If applicator placement is not within the acceptable tolerances of the planned position, the applicators may either be repositioned to be within acceptable tolerances of the planned position or the plan may be modified to use the applicators in their current out-of-tolerance position. The plan modification may include modifying a non-positional aspect of the plan (e.g. thermal ablation applicator power level or thermal ablation delivery time). Modifying the plan at this stage may be preferable to repositioning the applicators since repositioning the applicators may involve removing and replacing the applicators within the VOI, a potentially invasive process. The plan may be modified in several ways to accommodate the out-of-tolerance applicator position. For example, power levels during the thermal ablation, duration of delivery of thermal ablation, the planned coagulation necrosis volume and/or the positions of subsequent applicators may be modified to accommodate the out-of-tolerance applicator position.

Once the selected applicators are positioned, the thermal ablation may be delivered 515 via the positioned applicators as per the thermal ablation plan. The next step may be to monitor 516 the thermal ablation. This monitoring may be performed using one or more methods. For example, the thermal ablation applicators may be equipped with temperature sensors to sense temperatures in areas surrounding the applicators. Temperature probes may be used to measure temperatures at various locations within the VOI. Ultrasound equipment or ultrasound equipment with ARFI or elastography mode capabilities may be used to detect changes within the VOI. Ultrasound equipment may be able to detect significant changes within the VOI such as, for example, localized boiling due to the application of heat. Ultrasound equipment with ARFI or elastography mode capabilities may be able to detect changes in the mechanical properties of tissue or structures within the VOI and from that information infer temperature changes.

As the thermal ablation is being monitored 516, any changes detected may be compared 517 to expected changes as predicted by the thermal ablation plan. If any changes occur in the VOI indicating temperature or tissular changes beyond a predetermined level relative to the thermal ablation plan, an additional C-arm CBCT scanner imaging cycle starting at step 519 may be initiated. Additionally, if a predetermined amount of thermal ablation has been delivered 518, an additional C-arm CBCT scanner imaging cycle starting at step 519 may be initiated. If no changes have occurred within the VOI beyond a predetermined level relative to the thermal ablation plan and the predetermined amount of thermal ablation has not been delivered, the thermal ablation procedure may continue at step 513 according to the thermal ablation plan. In this manner, as thermal ablation is being performed, the loop comprising of steps 513 through 518 may be performed continuously. For example, the thermal ablation may be monitored 516 and continuously compared to the expected results from the thermal ablation plan 517 as the thermal ablation is being delivered. As long as no unexpected changes beyond a predetermined level relative to the thermal ablation plan have occurred or a predetermined amount of time has not passed, it may reasonably be assumed that the thermal ablation is proceeding within acceptable tolerances according to the thermal ablation plan.

Thus, unexpected changes beyond a predetermined level detected by the monitoring 516 or the passage of a predetermined amount of time 518 may trigger and an additional C-arm CBCT scanner imaging cycle which starts with positioning 519 the C-arm CBCT scanner so that the VOI is within the field of view of the scanner. An imaging cycle may then take place similar to the imaging cycle described previously at steps 504 through 507. That is, once the C-arm CBCT scanner is in position 519, the next step may be to illuminate 520 the VOI the conical beam of x-rays, then detect 521 x-rays that have passed through the VOI with the two-dimensional x-ray detector array. This imaging cycle may be repeated until 522 enough information has been gathered to render a three-dimensional view of the VOI at which point, a three-dimensional temperature differential (TD) image data set for the VOI may be computed 523.

Once a three-dimensional temperature differential image data set is generated, the process of generating an inferred temperature changes (ITC) image may take place. The first step in the process is to decide 524 whether to use a static reference, such as the baseline image data set, or a dynamic reference, such as the previously captured temperature differential image data set, when creating the inferred temperature changes image data set.

If a static reference is selected, the next step may be to calculate 525 the inferred temperature changes image data set from the most recent temperature differential image data set and the baseline image data set. This calculation may involve comparing values at corresponding spatial locations of the temperature differential image data set and the baseline image data set. The values for the spatial locations within the image data sets may be in the form of Hounsfield unit data obtained from the C-arm CBCT scanner. By using the methods described above, the Hounsfield unit data changes may be used to infer temperature changes throughout the VOI to create the inferred temperature changes image data set. Once the inferred temperature changes image data set based on a static reference is created, the next step may be to display 526 the inferred temperature changes image data set.

If, in step 524, a dynamic reference was selected, the next step may be to select 527 the temperature differential image data set for use as the dynamic reference image data set in the process of creating an inferred temperature changes image data set. Any temperature differential image data set captured during the thermal ablation procedure may be used as the dynamic reference. The system controller may be configured to use the previously captured temperature differential image data set to create the inferred temperature changes image data set. In this regard, after each temperature differential image data set is created, an inferred temperature changes image data set will be created 528 containing data of temperature changes between the last two image capture sequences. Once the inferred temperature changes image data set based on a dynamic reference is created, the next step may be to display 526 the inferred temperature changes image data set.

The inferred temperature changes image data set may contain inferred temperature changes for each spatial location within the VOI relative to the selected reference image (i.e., static or dynamic). The display 526 may be in the form of colored isothermal regions overlaid over an image of the VOI or a portion of the VOI. In addition, the display 526 may include a demarcation or indication of a predicted coagulation necrosis volume based on the thermal ablation applied to the VOI up to the current point in the thermal ablation procedure. Also, the physician may choose to change the reference image used for the generation of the inferred temperature changes image data set, thereby returning the process to step 524 and subsequently generating an additional inferred temperature changes image data set.

The next step may be to compare 529 the predicted coagulation necrosis volume to the coagulation necrosis goals of the thermal ablation plan. This comparison 529 may be made by the system controller, the physician (by reviewing the display of the predicted necrosis volume), or both.

If it is determined that the coagulation necrosis goals have been met, the next step may be to remove 530 any thermal ablation applicators from the patient. This may be followed by a continued monitoring 531 of temperatures within the VOI until temperatures within the VOI returned to within a predetermined level relative to normal body temperature. The thermal ablation procedure may then be ended 532.

If, in step 529, it is determined that the coagulation necrosis goals have not been met, the next step may be to compare 533 the inferred temperature changes image data set to the expected temperature changes from the thermal ablation plan. Inferred temperature changes image data sets created with either static or dynamic references may be used for this comparison. This comparison may then be displayed 534. This display may communicate to the physician how the thermal ablation procedure is proceeding relative to the thermal ablation plan.

Next, a determination is made as to whether or not the thermal ablation procedure is progressing 535 within acceptable limits relative to the thermal ablation plan. The thermal ablation plan may include expected temperature changes at substantially each spatial location within the array as a function of time during the thermal ablation procedure. Furthermore, the plan may also include one or more additional parameters selected from the following group:

target coagulation necrosis volume;
  planned coagulation necrosis volume;
  thermal ablation applicator quantity;
  thermal ablation applicator type or types;
  thermal ablation applicator power level (for each applicator);
  thermal ablation applicator position (for each applicator);
  thermal ablation applicator target (for each applicator);
  temperature differential image triggering parameters; and
  supplemental imaging modalities;
  patient positioning; and
  temperature differential image capture schedule.

Other parameters used in planning medical procedures known to those skilled in the art (e.g. location and time of the procedure, surgical personnel required and medications or anesthesia to be administered) may also be included in the thermal ablation plan.

This determination of whether the thermal ablation procedure is progressing 535 within acceptable limits may be performed by the system controller and then presented to the physician for approval. For example, the system controller may make a determination that the thermal ablation procedure is proceeding according to the thermal ablation plan within an acceptable margin and present this information to the physician at which point the physician may agree with the system controller or override the determination of the system controller. This determination may be made (by the system controller and/or the physician) on the basis of a comparison of the propagation of measured temperature changes relative to the expected temperature changes from the thermal ablation plan.

If the physician determines that the measured temperature changes are within an acceptable margin, the thermal ablation procedure may continue by returning to step 513 without altering the thermal ablation plan. This determination by the physician may be a result of the physician agreeing with the determination by the system controller or it may be a result of the physician overriding a determination by the system controller that the original thermal ablation plan should be modified prior to proceeding. In another embodiment, the system controller may simply present the information to the physician and the entire comparison and determination of whether or not to proceed with the thermal ablation plan as originally constructed may be made by the physician.

If the determination 535 is made that the measured temperature changes are not within an acceptable margin, the thermal ablation plan may be updated 536. This update may include alteration of any or all of the thermal ablation plan parameters to produce an updated or new plan. For example, during the first pass through the flowchart of FIG. 5B, the determination step 535 may compare the progress of the thermal ablation procedure to the original or first thermal ablation plan. If the thermal ablation is not progressing within acceptable limits according to the first thermal ablation plan, the first plan may be updated 536 to produce a second thermal ablation plan. These updates to the first thermal ablation plan may include altering or regenerating any or all of the parameters of the first thermal ablation plan to produce the second thermal ablation plan. On subsequent passes through the process loop containing the comparison step 535, additional thermal ablation plans may be created (and then followed) by updating 536 those plans if needed. Following the updating 536 of the thermal ablation plan to a subsequent thermal ablation plan, the thermal ablation procedure may continue by returning to step 513 and following the updated thermal ablation plan. The thermal ablation plan may be updated by the system controller or by the physician. In either case, the updates to the thermal ablation plan may take into account unexpected thermal properties of structures or tissue within the VOI. For example, temperature changes within the VOI due to the application of thermal ablation may not have proceeded as rapidly as predicted due to higher-than-expected levels of perfusion. To account for this, the thermal ablation plan may, for example, be modified by increasing the power level of one or more applicators, by repositioning one or more applicators, or by altering any other parameter of the thermal ablation plan.

From step 513, the thermal ablation procedure may continue by stepping through the process discussed above subsequent to step 513 until the coagulation necrosis goals have been met (that decision being made at step 529) and the thermal ablation procedure is ended 532.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method of performing a thermal ablation procedure within a Volume Of Interest (VOI) in a patient comprising the steps of:
    (a) capturing a baseline digital image with an x-ray system of a VOI in a patient, wherein said baseline digital image is comprised of a first set of detected image signal data corresponding with each spatial location in an array of spatial locations throughout said VOI;
    (b) performing a thermal ablation procedure on at least a first sub-volume of said VOI according to a first thermal ablation plan, wherein said first thermal ablation plan comprises expected temperature changes at each said spatial location within said array of spatial locations as a function of time during said thermal ablation procedure;

(c) capturing a first temperature differential digital image with said x-ray system of said VOI multiple times during said thermal ablation procedure, wherein each said first temperature differential digital image is comprised of a corresponding second set of detected image signal data corresponding with each said spatial location in said array of spatial locations throughout said VOI;

(d) registering each said first temperature differential digital image to said baseline digital image;

(e) inferring, based at least in part on said baseline digital image and each said first temperature differential digital image, an amount of temperature change at each of said multiple times at each said spatial location within said array of spatial locations throughout said VOI; and (f) comparing said inferred temperature changes at said multiple times at each said spatial location within said array to said expected temperature changes at each said spatial location within said array as a function of time during said thermal ablation.

2. A method as set forth in claim 1, wherein said first thermal ablation plan further comprises at least one additional parameter selected from a group consisting of:
thermal ablation applicator quantity;
thermal ablation applicator types;
thermal ablation applicator power level;
thermal ablation applicator position;
thermal ablation applicator target;
temperature differential image triggering parameters;
supplemental imaging modalities;
patient positioning; and
temperature differential image capture schedule.

3. A method as set forth in claim 2, wherein said first thermal ablation plan further comprises a plurality of parameters from said group.

4. A method as set forth in claim 1, wherein said patient remains substantially stationary throughout said thermal ablation procedure.

5. A method as set forth in claim 1 further comprising:
positioning a patient on a bed prior to said capturing said baseline digital image;
maintaining said position of said patient relative to said bed during and between all steps of said thermal ablation procedure subsequent to said positioning step,
wherein said patient and bed are not moved substantially more than a maximum lineal dimension of said VOI during and between all steps of said thermal ablation procedure subsequent to said positioning step.

6. A method as set forth in claim 1, further comprising:
retrieving said first thermal ablation plan from a memory storage module prior to performing thermal ablation.

7. A method as set forth in claim 1, wherein said capturing of said baseline digital image comprises:
illuminating said VOI with x-rays;
detecting a plurality of portions of said x-rays that passed through said VOI; and
at least partially generating said baseline digital image based on said detected x-rays.

8. A method as set forth in claim 7, further comprising calibrating said baseline digital image, said calibration comprising:
measuring temperature of at least a first spatial location within said VOI; and
correlating said measured temperature at said at least first spatial location within said VOI to said baseline digital image at said at least first spatial location within said VOI.

9. A method as set forth in claim 7, wherein said illuminating and said detecting are performed with an x-ray Computed Tomography (CT) scanner.

10. A method as set forth in claim 7, wherein said illuminating and detecting are performed with an x-ray CT C-arm scanner.

11. A method as set forth in claim 7, wherein said illuminating is performed with a conical x-ray beam.

12. A method as set forth in claim 7, wherein said illuminating is dynamically shaped by at least one multi-leaf collimator.

13. A method as set forth in claim 7, further comprising at least partially generating said baseline digital image using at least one of the methods selected from a group consisting of:
ultrasound, ultrasound with ARFI capabilities, ultrasound with elastography capabilities, PET, SPECT, and MRI.

14. A method as set forth in claim 7, wherein said capturing said baseline digital image further comprises:
capturing supplemental information about said VOI using a supplemental imaging modality; and
employing software to enhance said supplemental information.

15. A method as set forth in claim 14, wherein said supplemental imaging modality is selected from a group consisting of:
ultrasound, ultrasound with ARFI capabilities, ultrasound with elastography capabilities, PET, SPECT, and MRI.

16. A method as set forth in claim 15, wherein said supplemental imaging modality further comprises:
using at least one contrast agent.

17. A method as set forth in claim 1, further comprising:
spatially filtering said baseline digital image.

18. A method as set forth in claim 17, wherein said spatially filtering said baseline digital image is performed with a Gaussian filter.

19. A method as set forth in claim 1, further comprising:
automatically identifying structures within said baseline digital image.

20. A method as set forth in claim 1, wherein each spatial location is a voxel representing a volume of at most 1 $cm^3$.

21. A method as set forth in claim 20, wherein each voxel represents a volume of at most 1 $mm^3$.

22. A method as set forth in claim 1, further comprising:
spatially displaying said baseline digital image.

23. A method as set forth in claim 1, further comprising:
accessing a preliminary thermal ablation plan, wherein said preliminary thermal ablation plan comprises expected temperature changes at substantially each spatial location within said array as a function of time during said thermal ablation; and
comparing said baseline digital image to said preliminary thermal ablation plan.

24. A method as set forth in claim 23, wherein said preliminary thermal ablation plan further comprises at least one additional parameter selected from a group consisting of:
thermal ablation applicator quantity;
thermal ablation applicator types;
thermal ablation applicator power level;
thermal ablation applicator position;
thermal ablation applicator target;
temperature differential image triggering parameters;

supplemental imaging modalities;
patient positioning; and
temperature differential image capture schedule.

25. A method as set forth in claim 24, wherein said preliminary thermal ablation plan further comprises a plurality of parameters from said group.

26. A method as set forth in claim 23, further comprising:
employing software to register said baseline digital image to an image from said preliminary thermal ablation plan without the use of artificial fiducial markers.

27. A method as set forth in claim 26, further comprising:
spatially displaying said baseline digital image along with a planned thermal distribution throughout said VOI at a selectable point of said first thermal ablation plan, wherein said planned thermal distribution throughout said VOI is visually discernable.

28. A method as set forth in claim 26, further comprising:
spatially displaying said baseline digital image along with a planned coagulation necrosis target volume.

29. A method as set forth in claim 23, further comprising:
modifying said preliminary plan to produce said first thermal ablation plan based, at least in part, on said comparison of said baseline digital image to said preliminary thermal ablation plan.

30. A method as set forth in claim 1, wherein said performing thermal ablation further comprises:
positioning at least one thermal ablation applicator; and
modifying a non-positional aspect of said first thermal ablation plan based on said positioned at least one thermal ablation applicator.

31. A method as set forth in claim 1, wherein said performing thermal ablation is performed using a mode of thermal ablation delivery selected from a group consisting of:
RFA, laser ablation, microwave, extracorporeal focused ultrasound ablation, direct focused ultrasound ablation, and cryoablation.

32. A method as set forth in claim 31, wherein said performing thermal ablation is performed using a plurality of modes of thermal ablation delivery selected from said group.

33. A method as set forth in claim 1, further comprising:
using a stereotactic location system to aid a user in the positioning of a thermal ablation applicator into a position to deliver said thermal ablation.

34. A method as set forth in claim 1, further comprising:
using an automated insertion system to insert a thermal ablation applicator into a position to deliver said thermal ablation.

35. A method as set forth in claim 1, further comprising:
displaying a real-time image of said VOI wherein a current position of at least one thermal ablation applicator is visually discernable, wherein said real-time image is generated by at least one of CT and ultrasound;
registering said real-time image to a planning image of said VOI from said first thermal ablation plan wherein a planned position of at least one thermal ablation applicator is visually discernable in said planning image;
displaying said registered real-time image and said planning image by overlaying one of said real-time image and said planning image over the other of said real-time image and said planning image; and
outputting data relating to a relative position of said at least one thermal ablation applicator relative to said planned position of said at least one thermal ablation applicator.

36. A method as set forth in claim 1, further comprising:
periodically measuring temperature at a predetermined location within said VOI; and
triggering said capturing of said first temperature differential digital image based at least in part on said periodic measuring.

37. A method as set forth in claim 1, further comprising:
periodically imaging a predetermined location within said VOI; and
triggering said capturing of said first temperature differential digital image based at least in part on said periodic imaging.

38. A method as set forth in claim 37, wherein said periodic imaging is performed by a method selected from a group consisting of:
ultrasound, ultrasound with ARFI capabilities, and ultrasound with elastography capabilities.

39. A method as set forth in claim 1, further comprising:
actively controlling the performance of the thermal ablation with a closed-loop feedback thermal ablation delivery control system.

40. A method as set forth in claim 1, wherein said capturing of said first temperature differential digital image comprises:
illuminating said VOI with x-rays;
detecting a plurality of portions of said x-rays that passed through said VOI; and
at least partially generating said first temperature differential digital image based on said detected x-rays.

41. A method as set forth in claim 40, further comprising calibrating said first temperature differential digital image, said calibration comprising:
measuring temperature of at least a first spatial location within said VOI; and
correlating said measured temperature at said at least first spatial location within said VOI to said first temperature differential digital image at said at least first spatial location within said VOI.

42. A method as set forth in claim 40, further comprising at least partially generating said first temperature differential digital image using at least one of the methods selected from a group consisting of:
ultrasound, ultrasound with ARFI capabilities, ultrasound with elastography capabilities, PET, SPECT, and MR.

43. A method as set forth in claim 40, wherein said capturing said baseline digital image further comprises:
capturing supplemental information about said VOI using a supplemental imaging modality; and
employing software to enhance said supplemental information.

44. A method as set forth in claim 43, wherein said supplemental imaging modality is selected from a group consisting of:
ultrasound, ultrasound with ARFI capabilities, ultrasound with elastography capabilities, PET, SPECT, and MRI.

45. A method as set forth in claim 44, wherein said supplemental imaging modality further comprises:
using at least one contrast agent.

46. A method as set forth in claim 1, further comprising:
spatially filtering said first temperature differential digital image.

47. A method as set forth in claim 1, further comprising:
displaying said first temperature differential digital image.

48. A method as set forth in claim 1, further comprising:
registering said baseline digital image to an external coordinate system; and
registering said first temperature differential digital image to said external coordinate system.

49. A method as set forth in claim 1, further comprising:
employing software to register said first temperature differential digital image to said baseline digital image without the use of artificial fiducial markers.

50. A method as set forth in claim 1, further comprising:
calculating image signal data changes between said baseline digital image and said first temperature differential digital image for substantially each spatial location within said array of spatial locations.

51. A method as set forth in claim 50, wherein said calculating determines Hounsfield Unit changes for substantially each spatial location within said array of spatial locations.

52. A method as set forth in claim 1, further comprising:
calculating a predicted coagulation necrosis volume based, at least in part, on said inferred amount of temperature change at substantially each spatial location within said array of spatial locations.

53. A method as set forth in claim 52, further comprising:
displaying said predicted coagulation necrosis volume.

54. A method as set forth in claim 52, further comprising:
comparing said predicted coagulation necrosis volume to a planned coagulation necrosis volume.

55. A method as set forth in claim 1, further comprising:
displaying said temperature changes in the form of isothermal regions wherein said isothermal regions represent temperature ranges of at most 15° C.

56. A method as set forth in claim 55, wherein said isothermal regions represent temperature ranges of at most 1° C.

57. A method as set forth in claim 1, further comprising:
displaying an image of at least a portion of said VOI in which said inferred temperature changes are visually discernable.

58. A method as set forth in claim 57, further comprising:
displaying at least a portion of said image of at least a portion of said VOI as shaded isothermal three-dimensional volumes within said VOI.

59. A method as set forth in claim 57, further comprising:
displaying at least a portion of said image of at least a portion of said VOI as a selectable two-dimensional slice through said VOI.

60. A method as set forth in claim 57, further comprising:
displaying at least a portion of said image of at least a portion of said VOI as isothermal regions in a selectable two-dimensional slice through said VOI.

61. A method as set forth in claim 57, further comprising:
displaying at least a portion of said image of at least a portion of said VOI in a Multi-Planar Reformatted display.

62. A method as set forth in claim 57, further comprising:
displaying at least a portion of said image of at least a portion of said VOI as a three-dimensional volume rendered display.

63. A method as set forth in claim 57, further comprising:
displaying said inferred temperature changes relative to a display of planned temperature changes from said first thermal ablation plan.

64. A method as set forth in claim 1, further comprising:
continuing thermal ablation according to at least a portion of said first thermal ablation plan.

65. A method as set forth in claim 1, further comprising:
(g) adjusting said first thermal ablation plan to create a second thermal ablation plan, wherein said adjusting is based at least in part on said comparison; and
(h) continuing thermal ablation on at least one of said first sub-volume within said VOI and a second sub-volume within said VOI according to at least a portion of said second thermal ablation plan, wherein said second plan comprises expected temperature changes at substantially each spatial location within said VOI as a function of time during said continuing thermal ablation.

66. A method as set forth in claim 65, wherein said second thermal ablation plan further comprises at least one additional parameter selected from a group consisting of:
thermal ablation applicator quantity;
thermal ablation applicator types;
thermal ablation applicator power level;
thermal ablation applicator position;
thermal ablation applicator target;
temperature differential image triggering parameters;
supplemental imaging modalities;
patient positioning; and
temperature differential image capture schedule.

67. A method as set forth in claim 66, wherein said second thermal ablation plan further comprises a plurality of parameters from said group.

68. A method as set forth in claim 65, further comprising:
storing said second thermal ablation plan in a memory module.

69. A method as set forth in claim 65, further comprising adjusting at least one of the following parameters:
thermal ablation applicator power,
thermal ablation applicator delivery direction, and
thermal ablation applicator target point.

70. A method as set forth in claim 65, further comprising:
adjusting thermal ablation applicator position.

71. A method as set forth in claim 65, further comprising:
adjusting position of a thermal ablation applicator position by a user.

72. A method as set forth in claim 65, further comprising:
adjusting position of a thermal ablation applicator position by a robotic system.

73. A method as set forth in claim 65, further comprising adjusting at least one of the following:
thermal ablation applicator quantity, and
thermal ablation applicator type.

74. A method as set forth in claim 65, further comprising:
adjusting thermal ablation in a closed-loop feedback control system.

75. A method as set forth in claim 65, wherein said first sub-volume is substantially the same as said second sub-volume.

76. A method as set forth in claim 65, further comprising:
performing steps b, c, d, e, f, g and h at least one additional time.

77. A method as set forth in claim 65, further comprising:
performing steps b, c, d, e, f, g and h until a coagulation necrosis goal is achieved.

78. A method as set forth in claim 65, wherein said first sub-volume is substantially different than said second sub-volume.

79. A method as set forth in claim 1, further comprising:
capturing at least one additional temperature differential digital image;
registering said at least one additional temperature differential digital image to a previously captured digital image, wherein said previously captured digital image is a previously captured temperature differential digital image;
inferring an amount of temperature change at substantially each spatial location within said array of spatial locations between said previously captured digital image and said at least one additional temperature differential digital image; and
performing additional thermal ablation.

80. A method as set forth in claim 1, further comprising: performing steps b, c, d, e and f until a coagulation necrosis goal is achieved.

81. A method as set forth in claim 1, further comprising: generating a post-procedure report describing the performed thermal ablation.

82. A method as set forth in claim 81, wherein said post-procedure report at least partially conforms to the DICOM standard.

83. A method of performing a thermal ablation procedure within a Volume Of Interest (VOI) in a patient comprising the steps of:
    (aa) positioning a patient on a bed so that a VOI within said patient is within a field of view of an x-ray imaging device, wherein said imaging device encircles less than all of said VOI;
    (bb) capturing a baseline digital image of said VOI with said imaging device, wherein said baseline digital image is comprised of a first set of detected image signal data corresponding with each spatial location in an array of spatial locations throughout said VOI;
    (cc) performing thermal ablation on at least a first sub-volume of said VOI according to a first thermal ablation plan, wherein said first thermal ablation plan comprises expected temperature changes at each said spatial location within said array of spatial locations as a function of time during said thermal ablation procedure;
    (dd) capturing a first temperature differential digital image of said VOI with said x-ray imaging device multiple times during said thermal ablation procedure, wherein each said first temperature differential digital image is comprised of a corresponding second set of detected image signal data corresponding with each said spatial location in said array of spatial locations throughout said VOI;
    (ee) registering each said first temperature differential digital image to said baseline digital image;
    (ff) inferring, based at least in part on said baseline digital image and each said first temperature differential digital image, an amount of temperature change at each of said multiple times at each said spatial location within said array of spatial locations throughout said VOI; and
    (gg) comparing said inferred temperature changes at said multiple times at each said spatial location within said array to said expected temperature changes at each said spatial location within said array as a function of time during said thermal ablation; and,
    (hh) maintaining said position of said patient relative to said bed during and between each of said capturing of said baseline digital image, said performing thermal ablation, and said capturing of said first temperature differential digital image steps,
    wherein said patient and bed are not moved substantially more than a maximum lineal dimension of said VOI during and between each of said capturing of said baseline digital image, said performing thermal ablation, and said capturing of said first temperature differential digital image steps.

84. A method as set forth in claim 83, wherein said patient remains substantially stationary throughout said thermal ablation procedure.

85. A method as set forth in claim 83, further comprising: accessing said thermal ablation plan, wherein said plan comprises expected temperature changes at substantially each spatial location within said array as a function of time during said thermal ablation.

86. A method as set forth in claim 85, wherein said accessing is from a memory storage module.

87. A method as set forth in claim 85, further comprising: adjusting said thermal ablation plan based at least in part on differences between said baseline digital image and said first temperature differential digital image; and
continuing thermal ablation after said capturing of said first temperature differential image on at least one of said first sub-volume within said VOI and a second sub-volume within said VOI.

88. A method as set forth in claim 87, wherein said plan further comprises at least one additional parameter selected from a group consisting of:
    thermal ablation applicator quantity;
    thermal ablation applicator types;
    thermal ablation applicator power level;
    thermal ablation applicator position;
    thermal ablation applicator target;
    temperature differential image triggering parameters;
    supplemental imaging modalities;
    patient positioning; and
    temperature differential image capture schedule.

89. A method as set forth in claim 88, wherein said plan further comprises a plurality of parameters from said group.

90. A method as set forth in claim 87, wherein said adjusting said thermal ablation plan creates an adjusted thermal ablation plan, said method further comprising:
    storing said adjusted thermal ablation plan in a memory module.

91. A method as set forth in claim 83, wherein said imaging device is capable of illuminating a VOI with a conical beam of x-rays, wherein said beam of x-rays is detected by a two-dimensional flat panel sensor array.

92. A method as set forth in claim 83, further comprising calibrating said baseline digital image, said calibration comprising:
    measuring temperature of at least a first spatial location within said VOI; and
    correlating said measured temperature at said at least first spatial location within said VOI to said baseline digital image at said at least first spatial location within said VOI.

93. A method as set forth in claim 83, further comprising calibrating said first temperature differential digital image, said calibration comprising:
    measuring temperature of at least a first spatial location within said VOI; and
    correlating said measured temperature at said at least first spatial location within said VOI to said first temperature differential digital image at said at least first spatial location within said VOI.

94. A method as set forth in claim 83, wherein said performing thermal ablation is performed using a mode of thermal ablation delivery selected from a group consisting of:
    RFA, laser ablation, microwave, extracorporeal focused ultrasound ablation, direct focused ultrasound ablation, and cryoablation.

95. A method as set forth in claim 94, wherein said performing thermal ablation is performed using a plurality of modes of thermal ablation delivery selected from said group.

96. A method as set forth in claim 83, further comprising adjusting at least one of the following parameters:
    thermal ablation applicator power,
    thermal ablation applicator delivery direction, and
    thermal ablation applicator target point.

97. A method as set forth in claim 83, further comprising: adjusting thermal ablation applicator position.

98. A method as set forth in claim 83, further comprising:
adjusting position of a thermal ablation applicator position by a user.

99. A method as set forth in claim 83, further comprising:
adjusting position of a thermal ablation applicator position by a robotic system.

100. A method as set forth in claim 83, further comprising adjusting at least one of the following:
thermal ablation applicator quantity, and
thermal ablation applicator type.

101. A method as set forth in claim 83, further comprising:
adjusting thermal ablation in a closed-loop feedback control system.

102. A method as set forth in claim 83, further comprising:
capturing at least one additional temperature differential digital image;

registering said at least one additional temperature differential digital image to a previously captured digital image, wherein said previously captured digital image is a previously captured temperature differential digital image;

inferring an amount of temperature change at substantially each spatial location within said VOI between said previously captured digital image and said at least one additional temperature differential digital image; and performing additional thermal ablation.

103. A method as set forth in claim 83, further comprising:
performing steps cc, dd, and ee until a coagulation necrosis goal is achieved.

* * * * *